(12) United States Patent
Abramson et al.

(10) Patent No.: US 8,933,129 B2
(45) Date of Patent: Jan. 13, 2015

(54) COMPOUNDS AND METHODS FOR MODULATING ACTIVITY OF CALCIUM RELEASE CHANNELS

(75) Inventors: Jonathan Abramson, Portland, OR (US); Robert Strongin, Portland, OR (US)

(73) Assignee: State of Oregon by and through the State Board of Higher Education on behalf of Portland State University, Portland, OR (US)

( * ) Notice: Subject to any disclaimer, the term of this patent is extended or adjusted under 35 U.S.C. 154(b) by 384 days.

(21) Appl. No.: 13/264,055

(22) PCT Filed: Apr. 15, 2010

(86) PCT No.: PCT/US2010/001152
§ 371 (c)(1),
(2), (4) Date: Jan. 9, 2012

(87) PCT Pub. No.: WO2010/120382
PCT Pub. Date: Oct. 21, 2010

(65) Prior Publication Data
US 2012/0101085 A1    Apr. 26, 2012

Related U.S. Application Data

(60) Provisional application No. 61/169,426, filed on Apr. 15, 2009.

(51) Int. Cl.
| | |
|---|---|
| *A61K 31/136* | (2006.01) |
| *A61K 31/085* | (2006.01) |
| *A61K 31/138* | (2006.01) |
| *C07C 215/28* | (2006.01) |
| *C07D 417/06* | (2006.01) |
| *A61K 31/554* | (2006.01) |
| *C07D 417/14* | (2006.01) |

(52) U.S. Cl.
CPC ............ *C07D 417/06* (2013.01); *A61K 31/554* (2013.01); *C07D 417/14* (2013.01)
USPC .......................................... 514/646; 514/718

(58) Field of Classification Search
CPC . A61K 31/136; A61K 31/085; A61K 31/138; C07C 215/28
USPC ................................................. 514/646, 718
See application file for complete search history.

(56) References Cited

U.S. PATENT DOCUMENTS 6,489,125 B1    12/2002    Marks et al.

FOREIGN PATENT DOCUMENTS

| CN | 1195522 | * 10/1998 |
|---|---|---|
| EP | 0 565 721 | 10/1993 |
| WO | WO 2005/037195 | 4/2005 |
| WO | WO 2005/094457 | 10/2005 |
| WO | WO 2007/024717 | 3/2007 |

OTHER PUBLICATIONS

Extended Search Report and Written Opinion, dated Sep. 21, 2012, issued in corresponding EP Application No. 10 76 4782.8.
Kaneko et al., "Pharmacological Characteristics and Clinical Applications of K201," Current Clinical Pharmacology, 4:126-131, May 2009.
Yamamoto et al., "Identification of Target Domains of the Cardiac Ryanodine Receptor to Correct Channel Disorder in Failing Hearts," Circulation, 117:762-772, Jan. 2008.
PCT Written Opinion of the International Searching Authority for International Application No. PCT/US2010/001152, completed Jul. 13, 2010, 10 pgs.
Office Action, dated Apr. 24, 2013, issued in corresponding EP Application No. 10 764 782.8.

* cited by examiner

*Primary Examiner* — Sreeni Padmanabhan
*Assistant Examiner* — Sahar Javanmard
(74) *Attorney, Agent, or Firm* — Klarquist Sparkman, LLP

(57) ABSTRACT

The present teachings provide compounds of Formulae I and II: and pharmaceutically acceptable salts, hydrates, complexes, esters, and prodrugs thereof, wherein $R^1$, $R^{1'}$, $R^2$, $R^{2'}$, $R^3$, $R^{3'}$, and X are as defined herein. The present teachings also provide methods of making the compounds of formulae I and II, and methods of treating RyR-associated conditions, disorders, and diseases that include administering a therapeutically effective amount of a compound of formula I or II to a subject in need thereof. In addition, the present teachings relate to methods of reducing the open probability of a ryanodine receptor, and methods of reducing $Ca^{2+}$ release across a ryanodine receptor (e.g., into the cytoplasm of a cell), by contacting a compound of formula I or II with a ryanodine receptor.

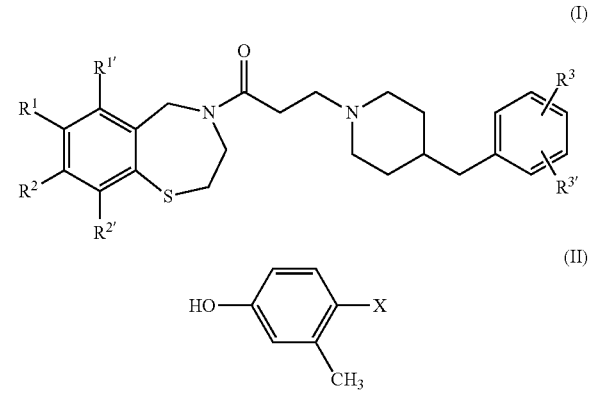

12 Claims, 8 Drawing Sheets

COMPOUNDS AND METHODS FOR MODULATING ACTIVITY OF CALCIUM RELEASE CHANNELS

CROSS REFERENCE TO RELATED APPLICATION

This application is a national phase application under 35 U.S.C. 371 of International Application No. PCT/US2010/001152, filed on Apr. 15, 2010, which claims priority to and the benefit of U.S. Provisional Application Ser. No. 61/169,426, filed on Apr. 15, 2009, the entire disclosures of each of which are incorporated herein in its entirety their entireties.

STATEMENT OF GOVERNMENT INTEREST

This invention was made with government support under Contract No. R01 AR 48911 awarded by the National Institutes of Health. The government has certain rights in the invention.

FIELD

This disclosure relates generally to compounds and methods for modulating the activity of calcium ion channels, including $Ca^{2+}$-induced (or $Ca^{2+}$-activated) calcium release channels and conformationally coupled calcium release channels such as ryanodine receptors in a subject.

BACKGROUND

The sarcoplasmic reticulum (SR) is a sub-cellular organelle responsible for regulating the $Ca^{2+}$ concentration in the cytosol of muscle fibers. By hydrolysis of ATP, the SR network lowers the free $Ca^{2+}$ concentration in the space surrounding the myofibrils to sub-micromolar levels, pumping $Ca^{2+}$ into the lumen of the SR. The reduction of myoplasmic free $Ca^{2+}$ concentration leads to muscle relaxation.

Muscle contraction is initiated by an action potential at the cell's surface membrane. This depolarization propagates down the transverse (T) tubules, which in turn triggers the release of $Ca^{2+}$ stored in the SR and contraction. More particularly, calcium release channels (CRCs) in the SR called ryanodine receptors (RyRs) open and release $Ca^{2+}$ from the SR into the intracellular cytoplasm of the cell. Release of $Ca^{2+}$ into the cytoplasm from the SR increases cytoplasmic $Ca^{2+}$ concentration. Open probability ($P_o$) of the RyR receptor refers to the likelihood that the RyR channel is open at any given moment, and therefore capable of releasing $Ca^{2+}$ into the cytoplasm from the SR.

There are three types of ryanodine receptors, all of which are highly-related $Ca^{2+}$ channels: RyR1, RyR2, and RyR3. RyR1 is found predominantly in skeletal muscle as well as other tissues, while RyR2 is found predominantly in the heart as well as other tissues, and RyR3 is found in the brain as well as other tissues. The RyR channels are formed by four RyR polypeptides in association with four FK506 binding proteins (FKBPs), specifically FKBP12 (calstabin1) and FKBP12.6 (calstabin2). Calstabin1 binds to RyR1, calstabin2 binds to RyR2, and calstabin1 binds to RyR3. The FKBP proteins (calstabin1 and calstabin2) bind to the RyR channel (one molecule per RyR subunit), stabilize RyR-channel functioning, and facilitate coupled gating between neighboring RyR channels, thereby preventing abnormal activation of the channel during the channel's closed state.

Important advances have been made toward understanding the 3-dimensional structure of the ryanodine receptor (RyR)/$Ca^{2+}$ release protein, and the possible functional role of other junctional SR proteins in excitation contraction coupling (ECC) in skeletal muscle. ECC differs in skeletal and cardiac muscle. In skeletal muscle, there appears to be a mechanical coupling between the dihydropyridine receptor (DHPR) found in the T-tubule membrane and the CRC or RyR found at the terminal end of the SR. In cardiac muscle, $Ca^{2+}$ enters the cell during the action potential through the DHPR, and initiates $Ca^{2+}$ release from the SR via a mechanism known as $Ca^{2+}$-induced $Ca^{2+}$ release. See e.g., Meissner, "Ryanodine receptor/$Ca^{2+}$ release channels and their regulation by endogenous effectors," Annu. Rev. Physiol. (1994), 56: 485-508; Dulhunty et al., "Ion channels in the sarcoplasmic reticulum of striated muscle," Acta. Physiol. Scand. (1996), 156: 375-85; Halling et al., "Regulation of voltage-gated $Ca^{2+}$ channels by calmodulin," Sci. STKE. (2005); 2005: re15; Coronado et al., "Structure and function of ryanodine receptors," Am. J. Physiol. (1994), 266: C1485-C1504; and Dulhunty et al., "Excitation-contraction coupling from the 1950s into the new millennium," Clin. Exp. Pharmacol. Physiol. (2006), 33: 763-72.

A number of associated proteins regulate the activity of the SR ryanodine receptors. The DHPR and RyR appear to form a hub for a large macromolecular complex, which includes triadin and calsequestrin (on the luminal face of the SR), FKBP12 (skeletal muscle) and FKBP12.6 (cardiac muscle), calmodulin, $Ca^{2+}$—CaM kinase (skeletal muscle), and protein kinase A (PKA) (cardiac muscle). Defective RyR-FKBP12.6 association has been implicated in heart failure, cardiomyopathy, cardiac hypertrophy, and exercise induced sudden cardiac death. It has been proposed that PKA phosphorylation of the cardiac RyR2 results in dissociation of FKBP12.6 from the $Ca^{2+}$ release channel, which results in an increased channel open probability ($P_o$), increased sensitivity to activation by $Ca^{2+}$, and destabilization of the CRC. Alternatively, it has been proposed that abnormal $Ca^{2+}$ handling by calsequestrin may lead to an increased $Ca^{2+}$ leak and cardiac arrhythmias. The cardio-protective agent K201 (also known as JTV519) and the antioxidant edaravone appear to correct the defective FKBP12.6 control of RyR2 and improve function. However, the mechanism of action of K201 is controversial. One report has shown that K201 suppresses spontaneous $Ca^{2+}$ release in ventricular myocytes independent of the presence of the FKBP12.6 protein, suggesting that the mode by which K201 decreases the $Ca^{2+}$ leak from cardiac SR does not involve the FKBP12.6 protein. See Hunt et al., "K201 (JTV519) suppresses spontaneous $Ca^{2+}$ release and [3H]ryanodine binding to RyR2 irrespective of FKBP12.6 association," Biochem. J. (2007), 404: 431-38.

In addition, CRCs from both cardiac and skeletal muscle SR are rich in thiol groups, and therefore, are strongly regulated by thiol reagents. It has been shown that oxidation of these thiol groups results in increased $Ca^{2+}$ release rates from SR vesicles, increased open probability of the reconstituted CRC, and increased high infinity ryanodine binding to the SR, while reduction of the disulfide(s) formed results in decreased activity. There are also a large number of non-thiol reagents known to either activate or inhibit RyR1 and/or RyR2. Among those compounds that activate the RyR/CRC are methylxanthines such as caffeine, plant alkaloids such as ryanodine, polyamines such as polylysine, quinone such as doxorubicin, and phenols such as 4-chloro-m-cresol (4-CmC). Among the non-thiol RyR/CRC inhibitors are local anesthetics such as tetracaine and procaine, the poly-unsaturated fatty acids such as docosahexaenoic acid (DHA). However, these reagents are physiologically and pharmacologically diverse, and their exact mode of action is not clear.

Accordingly, the art desires better understanding of calcium release mechanisms for developing a broader class of RyR/CRC activators and inhibitors.

SUMMARY

In light of the foregoing, it is an object of the present teachings to provide novel compounds and/or methods for regulating or modulating the activity of calcium release channels such as ryanodine receptors, in cells of a subject (e.g., mammals, preferably humans), thereby overcoming various deficiencies and shortcomings of the prior art, including those outlined above.

It can be an object of the present teachings to provide novel compounds and/or methods for inhibiting or decreasing intracellular calcium release, including calcium release in muscle cells (e.g., from sarcoplasmic reticulum in skeletal or cardiac muscle cells). These compounds and/or methods can include down-regulating or inhibiting the activity of calcium release channels such as ryanodine receptors.

It can be an object of the present teachings to provide compounds and/or methods for changing the redox potential of reactive thiols on ryanodine receptors in cells of a subject. Such redox potential changes can be achieved by modifying the thiol/disulfide balance within ryanodine receptors in cells of a subject, particularly, mammalian cells.

It can be an object of the present teachings to provide compounds and/or methods for treating or reducing the risk of a ryanodine receptor (RyR) associated disease, disorder, or condition in a subject. The RyR-associated disorder, disease, or condition can be a cardiac or skeletal muscle condition, disorder, or disease.

Accordingly, in part, the present teachings provide compounds of Formulae I and II:

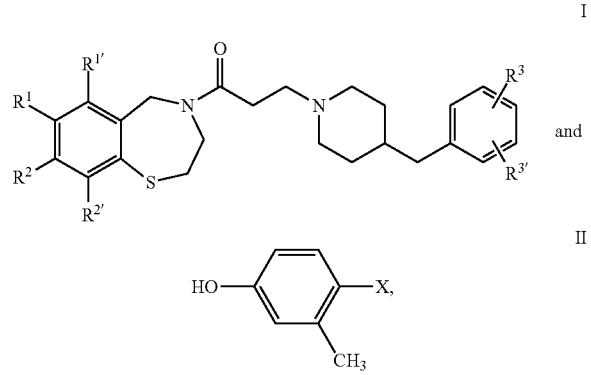

and pharmaceutically acceptable salts, hydrates, complexes, esters, and prodrugs thereof, wherein $R^1$, $R^{1'}$, $R^2$, $R^{2'}$, $R^3$, $R^{3'}$, and X are as defined herein.

The present teachings also provide methods of making the compounds of formulae I and II, and methods of treating RyR-associated conditions, disorders, and diseases comprising administering a therapeutically effective amount of a compound of formula I or II to a subject in need thereof. In addition, the present teachings relate to methods of reducing the open probability of a ryanodine receptor, and methods of reducing $Ca^{2+}$ release across a ryanodine receptor (e.g., into the cytoplasm of a cell), either of which can include contacting a compound of formula I or II with a ryanodine receptor.

The foregoing as well as other features and advantages of the present teachings will be more fully understood from the following figures, description, examples, and claims.

BRIEF DESCRIPTION OF DRAWINGS

It should be understood that the drawings described below are for illustration purpose only. The drawings are not necessarily to scale, with emphasis generally being placed upon illustrating the principles of the present teachings. The drawings are not intended to limit the scope of the present teachings in any way.

FIG. 3A: Control (50 μM $Ca^{2+}$), $P_o$=0.011; FIG. 3B: +6 mM Caffeine, $P_o$=0.071; FIG. 3C: +10 μM 4-MmC, $P_o$=0.015. Channel openings are directed down. Traces shown are 2 second-duration, $P_o$ are derived from 2 minute-traces. C—closed state, O—open state of channel. $P_o$=open probability.

FIG. 4A shows the reduction of the tetrazolium salt, 2,3-bis-(2-methoxy-4-nitro-5-sulphenyl)-(2H)-tetrazolium-5-carboxanilide (XTT) over time when reacted with 4-MmC at the following concentrations: 1 μM (○), 10 μM (▼), 20 μM (Δ), 100 μM (■), and 200 μM (□). Control data (●) are provided for comparison. FIG. 4B shows the initial rate of XTT reduction vs. [4-MmC].

FIG. 8A: Control (20 μM $Ca^{2+}$), $P_o$=0.107; FIG. 8B: +5 μM K201, $P_o$=0.060; FIG. 8C: +10 μM K201, $P_o$=0.047. Channel openings are directed down. Traces shown are 2 second-duration, $P_o$ are derived from 2 minute-traces. C—closed state, o—open state of channel. $P_o$=open probability.

FIG. 9A: Control (20 μM $Ca^{2+}$), $P_o$=0.032; FIG. 9B: +20 μM FK506, $P_o$=0.106; FIG. 9C: +10 μM K201, $P_o$=0.009. Channel openings are directed up. Traces shown are 2 second-duration, $P_o$ are derived from 2 minute-traces. C—closed state, O—open state of channel. $P_o$=open probability.

FIG. 10A: Control, $P_o$=0.83; FIG. 10B: 0.5 μM K201, $P_o$=0.42; FIG. 10C: 1.0 μM K201, $P_o$=0.014. Channel openings are directed down. Traces shown are 2 second-duration, $P_o$ are derived from 1 minute-traces. C represents the closed state, while $O_1$ and $O_2$ correspond to one or two open channels respectively.

FIG. 12A plots the transmembrane potential (Vm) and intracellular calcium level (Cai) over a 3-second period five minutes after administration of dofetilide (0.5 μM). FIG. 12B plots the transmembrane potential (Vm) and intracellular calcium level (Cai) over a 3-second period ten minutes after administration of dofetilide (0.5 μM). FIG. 12C plots the transmembrane potential (Vm) and intracellular calcium level (Cai) over a 3-second period six minutes after administration of dofetilide (0.5 μM) with the [1,3]dioxole derivative of K201 (1.0 μM). FIG. 12D plots the transmembrane potential (Vm) and intracellular calcium level (Cai) over a 3-second period nine minutes after administration of dofetilide (0.5 μM) with the [1,3]dioxole derivative of K201 (1.0 μM).

DETAILED DESCRIPTION

Figure 1:
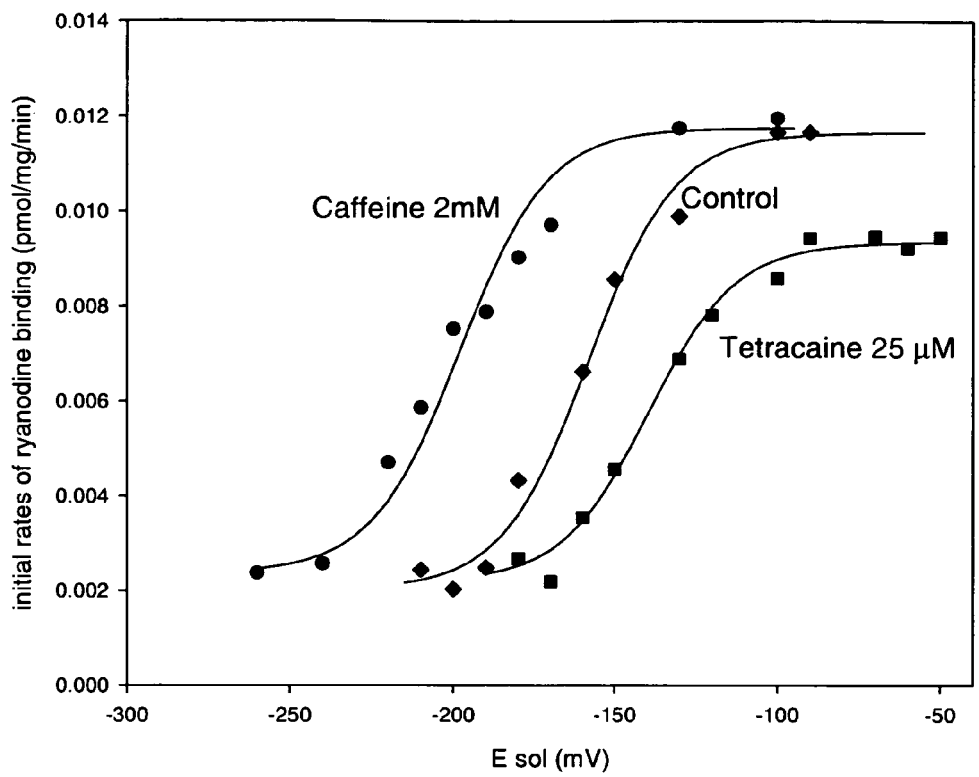
FIG. 1 plots the rate of ryanodine binding versus the redox potential (mV) of a control solution, a caffeine solution, and a tetracaine solution, where the redox potential of the solution is defined as: $E_{sol}=-240+(2.3 RT/nF)*\log_{10}[GSSG]/[GSH]^2$; where R is the gas constant, T is the temperature in K, n is the number of electrons transferred (n=2), F is the Faraday.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" or the symbol "~" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, a "compound" refers to the compound itself and its pharmaceutically acceptable salts, hydrates, complexes, esters, prodrugs and/or salts of prodrugs, unless otherwise understood from the context of the description or expressly limited to one particular form of the compound, i.e., the compound itself, or a pharmaceutically acceptable salt, hydrate, complex, ester, prodrug or salt of prodrug thereof.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein.

As used herein, "alkoxy" refers to —O-alkyl group. Examples of alkoxy groups include methoxy, ethoxy, propoxy (e.g., n-propoxy and isopropoxy), t-butoxy, pentoxyl, hexoxyl groups, and the like.

As used herein, "alkylthio" refers to an —S-alkyl group (which, in some cases, can be expressed as —S(O)$_w$-alkyl, wherein w is 0). Examples of alkylthio groups include methylthio, ethylthio, propylthio (e.g., n-propylthio and isopropylthio), t-butylthio, pentylthio, hexylthio groups, and the like.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_{6\text{-}20}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/ aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

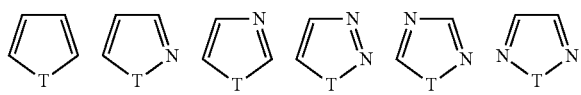

-continued

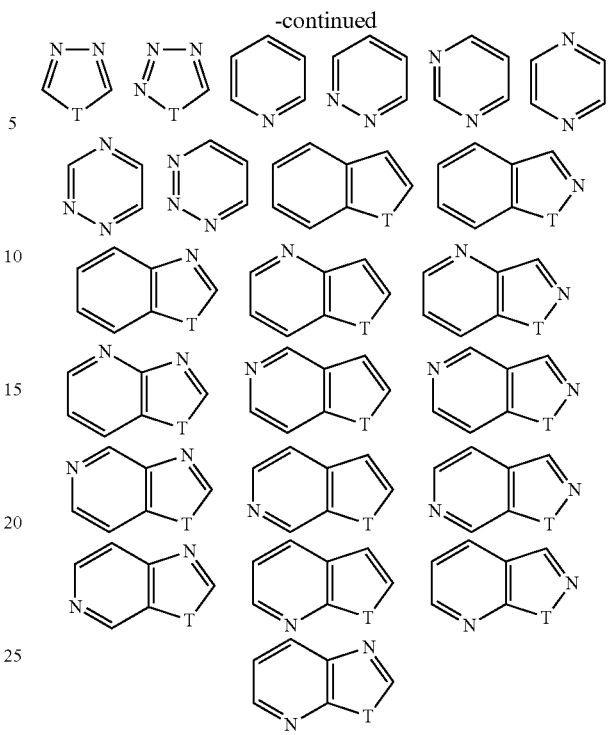

where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

Compounds of the present teachings can include a "divalent group" defined herein as a linking group capable of forming a covalent bond with two other moieties. For example, compounds of the present teachings can include a divalent $C_{1\text{-}20}$ alkyl group (e.g., a methylene group), a divalent $C_{2\text{-}20}$ alkenyl group (e.g., a vinylyl group), a divalent $C_{2\text{-}20}$ alkynyl group (e.g., an ethynylyl group). a divalent $C_{6\text{-}14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group). Generally, a chemical group (e.g., —Ar—) is understood to be divalent by the inclusion of the two bonds before and after the group.

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that is electrophilic and draws electrons to itself more than a hydrogen atom would if it occupied the same position in a molecule. Electron-withdrawing groups can be conjugated or not conjugated with the core molecule. Examples of electron-withdrawing groups include —$NO_2$, —CN, —NC, halogen or halo (e.g., F, Cl, Br, I), —$S(R^o)_2^+$, —$N(R^o)_3^+$, —$SO_3H$, —$SO_2R^o$, —$SO_3R^o$, —$SO_2NHR^o$, —$SO_2N(R^o)_2$, —COOH, —$COR^o$, —$COOR^o$, —$CONHR^o$, —$CON(R^o)_2$, $C_{1-40}$ haloalkyl groups, $C_{6-14}$ aryl groups, and 5-14 membered electron-poor heteroaryl groups; where $R^o$ is a $C_{1-20}$ alkyl group, a $C_{2-20}$ alkenyl group, a $C_{2-20}$ alkynyl group, a $C_{1-20}$ haloalkyl group, a $C_{1-20}$ alkoxy group, a $C_{6-14}$ aryl group, a $C_{3-14}$ cycloalkyl group, a 3-14 membered cycloheteroalkyl group, and a 5-14 membered heteroaryl group, each of which can be optionally substituted as described herein. For example, each of the $C_{1-20}$ alkyl group, the $C_{2-20}$ alkenyl group, the $C_{2-20}$ alkynyl group, the $C_{1-20}$ haloalkyl group, the $C_{1-20}$ alkoxy group, the $C_{6-14}$ aryl group, the $C_{3-14}$ cycloalkyl group, the 3-14 membered cycloheteroalkyl group, and the 5-14 membered heteroaryl group can be optionally substituted with 1-5 small electron-withdrawing groups such as F, Cl, Br, —$NO_2$, —CN, —NC, —$S(R^o)_2^+$, —$N(R^o)_3^+$, —$SO_3H$, —$SO_2R^o$, —$SO_3R^o$, —$SO_2NHR^o$, —$SO_2N(R^o)_2$, —COOH, —$COR^o$, —$COOR^o$, —$CONHR^o$, and —$CON(R^o)_2$.

It should be understood that the term "electron-donating group" can be used synonymously herein with "electron donor". In particular, an "electron-donating group" or an "electron-donor" refers to a functional group that donates electrons to a neighboring atom more than a hydrogen atom would if it occupied the same position in a molecule. Examples of electron-donating groups include chalcogen-containing groups such as —OH, —$OR^o$, —SH, —$SR^o$, and selenides, where $R^o$ is as defined above. Other electron-donating groups include nitrogen-containing groups such as optionally substituted amino groups (—$NH_2$, —$NHR^o$, —$N(R^o)_2$) and hydrazines, and 5-14 membered electron-rich heteroaryl groups. Other examples of electron-donating groups include electropositive groups which may work through non-resonance effects. Examples of such electropositive groups include silyl groups. Still, additional examples of electron-donating groups include saturated and unsaturated groups such as alkyl groups, alkenyl groups, aryl groups, and alkynyl groups which can increase electron-donating properties via both resonance and non-resonance effects and which can be optionally substituted with 1-4 groups independently selected from —OH, —$OR^o$, —SH, —$SR^o$, —$NH_2$, —$NHR^o$, —$N(R^o)_2$, and 5-14 membered electron-rich heteroaryl groups, where $R^o$ is as defined above.

Various unsubstituted heteroaryl groups can be described as electron-rich (or π-excessive) or electron-poor (or π-deficient). Such classification is based on the average electron density on each ring atom as compared to that of a carbon atom in benzene. Examples of electron-rich systems include 5-membered heteroaryl groups having one heteroatom such as furan, pyrrole, and thiophene; and their benzofused counterparts such as benzofuran, benzopyrrole, and benzothiophene. Examples of electron-poor systems include 6-membered heteroaryl groups having one or more heteroatoms such as pyridine, pyrazine, pyridazine, and pyrimidine; as well as their benzofused counterparts such as quinoline, isoquinoline, quinoxaline, cinnoline, phthalazine, naphthyridine, quinazoline, phenanthridine, acridine, and purine. Mixed heteroaromatic rings can belong to either class depending on the type, number, and position of the one or more heteroatom(s) in the ring. See Katritzky, A. R and Lagowski, J. M., *Heterocyclic Chemistry* (John Wiley & Sons, New York, 1960).

At various places in the present specification, substituents are disclosed in groups or in ranges. It is specifically intended that the description include each and every individual sub-combination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and diastereomers (geometric isomers). The present teachings include such optical isomers and diastereomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. For example, when a compound of the present teachings is a racemate, the racemate can be separated into the (S)-compound and (R)-compound by optical resolution. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

It is specifically contemplated that the depiction of one regioisomer includes any other regioisomers and any regioisomeric mixtures unless specifically stated otherwise.

As used herein, a "leaving group" ("LG") refers to a charged or uncharged atom (or group of atoms) that can be displaced as a stable species as a result of, for example, a substitution or elimination reaction. Examples of leaving groups include halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$ alkyl group or a $C_{6-14}$ aryl group each optionally substituted with 1-4 groups independently selected from a $C_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

Throughout the specification, structures may or may not be presented with chemical names. Where any question arises as to nomenclature, the structure prevails.

In one aspect, the present teachings provide derivatives of K201 (also known as JTV519), a cardio-protective agent that has the formula:

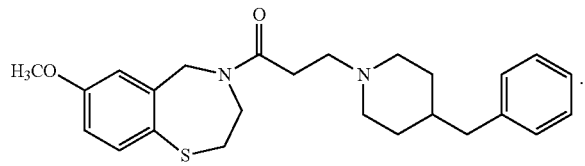

K201 (or JTV519)

The derivatives according to the present teachings include one or more-electron donating groups in addition to and/or in place of the methoxyl group at the C7 position of the 1,4-benzothiazepine moiety of the K201 compound. The present derivatives generally have enhanced electron-donating properties compared to K201. Applicants have found that such derivatives can act as $Ca^{2+}$ release channel (CRC) inhibitors, and that, unexpectedly, their inhibitory activity can be as high as 16 times that of K201.

More specifically, the present teachings provide compounds of Formula I:

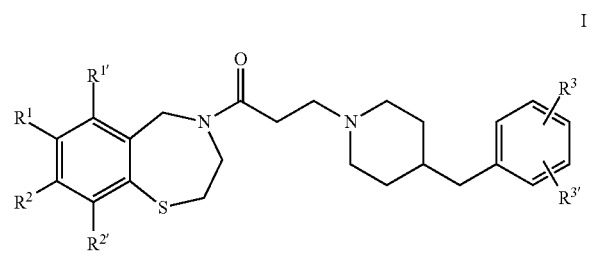

wherein:
$R^1$, $R^{1'}$, $R^2$, $R^{2'}$, $R^3$, and $R^{3'}$ independently are selected from H and an electron-donating group, provided that at least one of $R^1$, $R^{1'}$, $R^2$, $R^{2'}$, $R^3$, and $R^{3'}$ is not H; or alternatively, when $R^3$ and $R^{3'}$ are bonded to two adjacent carbon atoms, $R^3$ and $R^{3'}$, together with the two adjacent carbon atoms, form a 5-membered monocyclic moiety which is fused to the phenyl group and comprises 1-2 heteroatoms selected from O, S, and N,
provided that:
when each of $R^{1'}$, $R^2$, $R^{2'}$, $R^3$ and $R^{3'}$ is H, $R^1$ is an electron-donating group that is not —$OCH_3$; and
when $R^1$ is —$OCH_3$, at least one of $R^{1'}$, $R^2$, $R^{2'}$, $R^3$ and $R^{3'}$ is not H,
that is, the compound is not

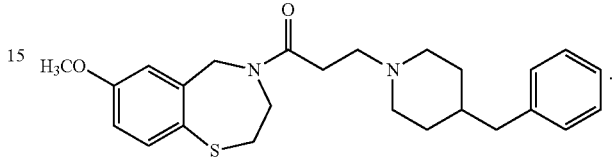

K201 (or JTV519)

In various embodiments, the electron-donating group can be selected from OH, $OR^4$, SH, $SR^4$, $NH_2$, $NHR^4$, $NR^4R^{4'}$, and a $C_{1-10}$ alkyl group optionally substituted with 1-4 groups independently selected from OH, $OR^4$, SH, $SR^4$, $NH_2$, $NHR^4$, and $NR^4R^{4'}$, where $R^4$ and $R^{4'}$ are identical or different $C_{1-10}$ alkyl groups. In some embodiments, the electron-donating group can be selected from OH, $OR^4$, $NH_2$, $NHR^4$, and $NR^4R^{4'}$, where $R^4$ and $R^{4'}$ are identical or different $C_{1-6}$ alkyl groups. For example, $R^4$ and $R^{4'}$ independently can be selected from a methyl group, an ethyl group, an n-propyl group, an iso-propyl group, an n-butyl group, an iso-butyl group, a sec-butyl group, a tert-butyl group, an n-pentyl group, an iso-pentyl group, and an neopentyl group.

In some embodiments, $R^1$ can be $OCH_3$, and $R^{1'}$, $R^2$, $R^{2'}$, $R^3$, and $R^{3'}$ independently can be selected from H and an electron-donating group, provided that at least one of $R^{1'}$, $R^2$, $R^{2'}$, $R^3$, and $R^{3'}$ is not H. That is, in embodiments where $R^1$ is $OCH_3$, at least one of $R^{1'}$, $R^2$, $R^{2'}$, $R^3$, and $R^{3'}$ is an electron-donating group, for example, an electron-donating group selected from OH, $OR^4$, SH, $SR^4$, $NH_2$, $NHR^4$, $NR^4R^{4'}$, and a $C_{1-10}$ alkyl group optionally substituted with 1-4 groups independently selected from OH, $OR^4$, SH, $SR^4$, $NH_2$, $NHR^4$, and $NR^4R^{4'}$, where $R^4$ and $R^{4'}$ are identical or different $C_{1-6}$ alkyl groups. In certain embodiments where $R^1$ is $OCH_3$, at least one of $R^2$ and $R^3$ can be an alkoxy group (e.g., $OCH_3$), and each of $R^{1'}$, $R^{2'}$, and $R^{3'}$ can be H. In other embodiments where $R^1$ is $OCH_3$ and at least one of $R^2$ and $R^3$ is an alkoxy group, at least one of $R^{1'}$, $R^{2'}$, and $R^{3'}$ can be an electron-donating group as described herein.

In some embodiments, $R^2$ can be an electron-donating group selected from OH, $OR^4$, SH, $SR^4$, $NH_2$, $NHR^4$, $NR^4R^{4'}$, and a $C_{1-10}$ alkyl group optionally substituted with 1-4 groups independently selected from OH, $OR^4$, SH, $SR^4$, $NH_2$, $NHR^4$, and $NR^4R^{4'}$; where $R^4$ and $R^{4'}$ are identical or different $C_{1-6}$ alkyl groups. In some of these embodiments, each of $R^1$, $R^{1'}$, $R^{2'}$, $R^3$, and $R^{3'}$ can be H. In other embodiments where $R^2$ is an electron-donating group, at least one of $R^1$, $R^{1'}$, $R^{2'}$, $R^3$, and $R^{3'}$ also can be an electron-donating group, for example, an electron-donating group selected from OH, $OR^4$, SH, $SR^4$, $NH_2$, $NHR^4$, $NR^4R^{4'}$, and a $C_{1-10}$ alkyl group optionally substituted with 1-4 groups independently selected from OH, $OR^4$, SH, $SR^4$, $NH_2$, $NHR^4$, and $NR^4R^{4'}$; where $R^4$ and $R^{4'}$ are identical or different $C_{1-6}$ alkyl groups. In certain embodiments where $R^2$ is an electron-donating group, at least one of $R^{1'}$, $R^{2'}$, $R^3$, and $R^{3'}$ independently can be selected from OH, $OR^4$, SH, $SR^4$, $NH_2$, $NHR^4$, $NR^4R^{4'}$, and a $C_{1-10}$ alkyl group optionally substituted with 1-4 groups independently selected from OH, $OR^4$, SH, $SR^4$, $NH_2$, $NHR^4$, and $NR^4R^{4'}$; where $R^4$ and $R^{4'}$ are identical or different $C_{1-6}$ alkyl groups, and $R^1$ can be H or an electron-donating group other than $OCH_3$.

In some embodiments, both $R^1$ and $R^2$ can be $OCH_3$, and each of $R^{1'}$, $R^{2'}$, $R^3$, and $R^{3'}$ independently can be selected from H and an electron-donating group. In certain embodiments, $R^{1'}$, $R^{2'}$, $R^3$, and $R^{3'}$ independently can be selected from H, OH, $OR^4$, SH, $SR^4$, $NH_2$, $NHR^4$, $NR^4R^{4'}$, and a $C_{1-10}$ alkyl group optionally substituted with 1-4 groups independently selected from OH, $OR^4$, SH, $SR^4$, $NH_2$, $NHR^4$, and $NR^4R^{4'}$, where $R^4$ and $R^{4'}$ are identical or different $C_{1-6}$ alkyl groups. In particular embodiments, at least one of $R^{1'}$, $R^{2'}$, $R^3$, and $R^{3'}$ is not H and can be selected from OH, $OR^4$, SH, $SR^4$, $NH_2$, $NHR^4$, and $NR^4R^{4'}$, where $R^4$ and $R^{4'}$ are as defined herein.

In some embodiments, at least one of $R^3$ and $R^{3'}$ can be an electron donating group. For example, at least one of $R^3$ and $R^{3'}$ can be selected from OH, $OR^4$, SH, $SR^4$, $NH_2$, $NHR^4$, $NR^4R^{4'}$, and a $C_{1-10}$ alkyl group optionally substituted with 1-4 groups independently selected from OH, $OR^4$, SH, $SR^4$, $NH_2$, $NHR^4$, and $NR^4R^{4'}$, where $R^4$ and $R^{4'}$ are identical or different $C_{1-6}$ alkyl groups. In some of these embodiments, each of $R^1$, $R^{1'}$, $R^2$, and $R^{2'}$ can be H. In other embodiments where at least one of $R^3$ and $R^{3'}$ is an electron donating group, at least one of $R^1$, $R^{1'}$, $R^2$, and $R^{2'}$ can be selected from OH, $OR^4$, SH, $SR^4$, $NH_2$, $NHR^4$, $NR^4R^{4'}$, and a $C_{1-10}$ alkyl group optionally substituted with 1-4 groups independently selected from OH, $OR^4$, SH, $SR^4$, $NH_2$, $NHR^4$, and $NR^4R^{4'}$, where $R^4$ and $R^{4'}$ are as defined herein.

In embodiments where each of $R^3$ and $R^{3'}$ is an electron donating group, $R^3$ and $R^{3'}$ can be substituted at meta, ortho, or para positions relative to each other. That is, the present compounds can have a formula selected from:

(1)
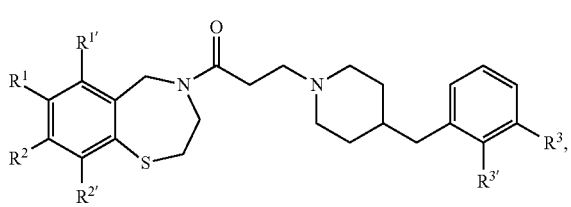

(2)
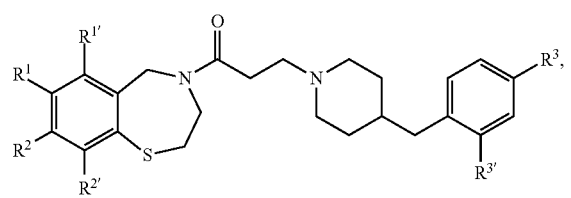

(3)
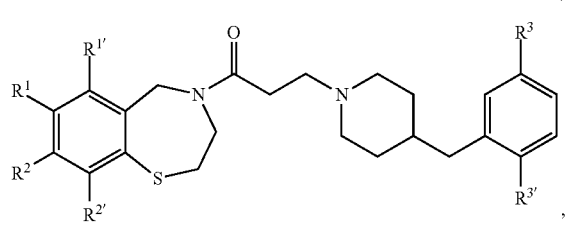

(4)
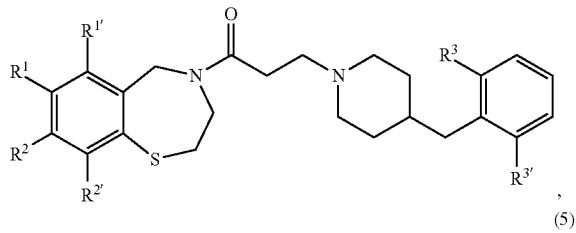

(5)
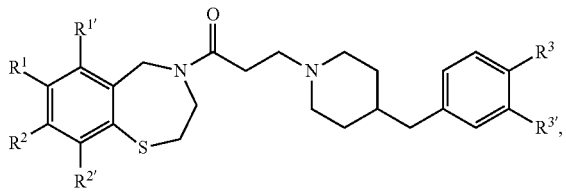

and (6)
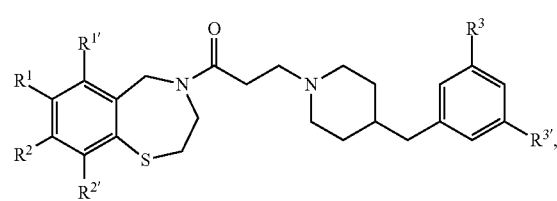

where each of $R^3$ and $R^{3'}$ independently can be selected from OH, $OR^4$, SH, $SR^4$, $NH_2$, $NHR^4$, $NR^4R^{4'}$, and a $C_{1-10}$ alkyl group optionally substituted with 1-4 groups independently selected from OH, $OR^4$, SH, $SR^4$, $NH_2$, $NHR^4$, and $NR^4R^{4'}$, where $R^4$ and $R^{4'}$ are identical or different $C_{1-6}$ alkyl groups, and $R^1$, $R^{1'}$, $R^2$, and $R^{2'}$ are as defined herein. For example, in some of these embodiments, each of $R^1$, $R^{1'}$, $R^2$, and $R^{2'}$ can be H. In some of these embodiments, at least one of $R^1$, $R^{1'}$, $R^2$, and $R^{2'}$ can be selected from OH, $OR^4$, SH, $SR^4$, $NH_2$, $NHR^4$, $NR^4R^{4'}$, and a $C_{1-10}$ alkyl group optionally substituted with 1-4 groups independently selected from OH, $OR^4$, SH, $SR^4$, $NH_2$, $NHR^4$, and $NR^4R^{4'}$, where $R^4$ and $R^{4'}$ are as defined herein. In some of these embodiments, $R^1$ can be $OCH_3$. In some of these embodiments, $R^1$ can be an electron-donating group other than $OCH_3$. In some of these embodiments, each of $R^1$ and $R^2$ can be $OCH_3$.

In other embodiments represented by any one of formulae (1)-(6), one of $R^3$ and $R^{3'}$ can be H, while the other of $R^3$ and $R^{3'}$ can be an electron donating group, for example, an electron-donating group selected from OH, $OR^4$, SH, $SR^4$, $NH_2$, $NHR^4$, $NR^4R^{4'}$, and a $C_{1-10}$ alkyl group optionally substituted with 1-4 groups independently selected from OH, $OR^4$, SH, $SR^4$, $NH_2$, $NHR^4$, and $NR^4R^{4'}$, where $R^4$ and $R^{4'}$ are identical or different $C_{1-6}$ alkyl groups. Accordingly, the present compounds can have a formula selected from:

(7)
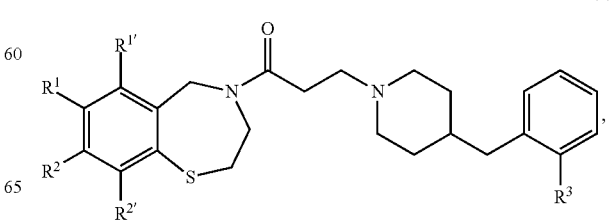

(8)

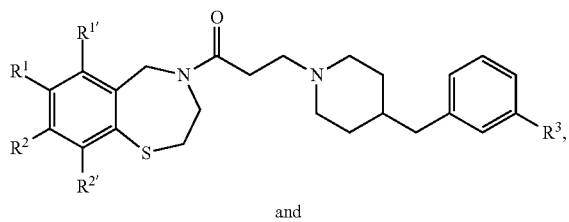

and (9)

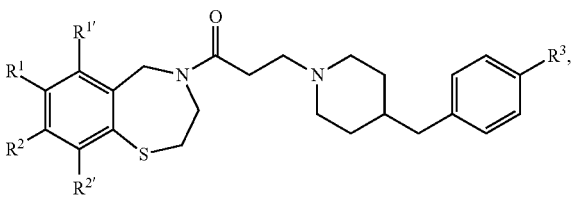

where one of $R^3$ and $R^{3\prime}$ is H, the other of $R^3$ and $R^{3\prime}$ is an electron donating group as described herein, and $R^1$, $R^{1\prime}$, $R^2$, and $R^{2\prime}$ are as defined herein. For example, in some of these embodiments, each of $R^1$, $R^{1\prime}$, $R^2$, and $R^{2\prime}$ can be H. In some of these embodiments, at least one of $R^1$, $R^{1\prime}$, $R^2$, and $R^{2\prime}$ can be selected from OH, $OR^4$, SH, $SR^4$, $NH_2$, $NHR^4$, $NR^4R^{4\prime}$, and a $C_{1-10}$ alkyl group optionally substituted with 1-4 groups independently selected from OH, $OR^4$, SH, $SR^4$, $NH_2$, $NHR^4$, and $NR^4R^{4\prime}$, where $R^4$ and $R^{4\prime}$ are as defined herein. In some of these embodiments, $R^1$ can be $OCH_3$. In some of these embodiments, $R^1$ can be an electron-donating group other than $OCH_3$. In some of these embodiments, each of $R^1$ and $R^2$ can be $OCH_3$.

In some embodiments, $R^3$ and $R^{3\prime}$, together with the two adjacent carbon atoms to which they are respectively bonded, can form a 5-membered cycloheteroalkyl or heteroaryl group which is fused to the phenyl group, thus providing an electron-rich benzofused moiety. For example, the 5-membered cycloheteroalkyl or heteroaryl group can be selected from:

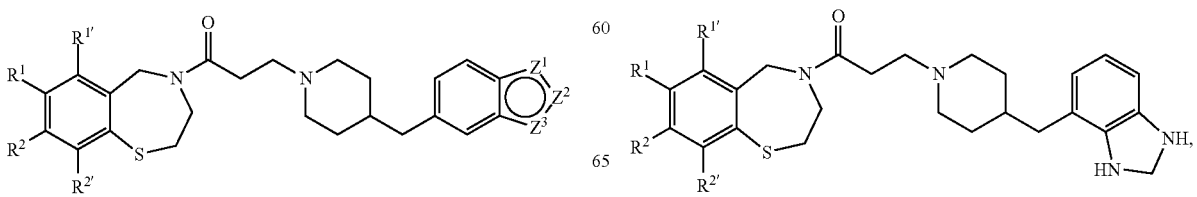

Accordingly, certain embodiments of the present compounds can be represented by Formula I' or I":

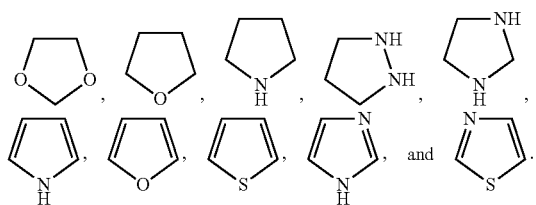

I'

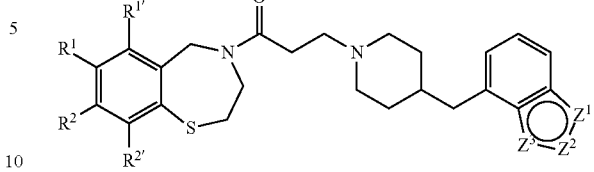

I"

where each of $R^1$, $R^{1\prime}$, $R^2$, and $R^{2\prime}$ independently is H or an electron-donating group, and $Z^1$, $Z^2$, and $Z^3$ independently are selected from O, NH, S, $CH_2$, =N—, and =CH—. In certain embodiments, $Z^1$, $Z^2$, and $Z^3$ independently can be selected from O, NH, S, and $CH_2$, thereby providing a benzofused-cycloheteroalkyl moiety. In other embodiments, $Z^1$, $Z^2$, and $Z^3$ independently can be selected from O, NH, S, $CH_2$, =N—, and =CH—, where at least one of $Z^1$, $Z^2$, and $Z^3$ is =N— or =CH—, thereby providing a benzofused-heteroaryl moiety.

For example, certain embodiments of compounds of Formulae I' and I" can be selected from:

(10)

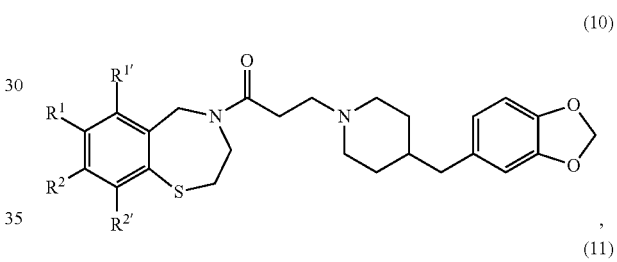

(11)

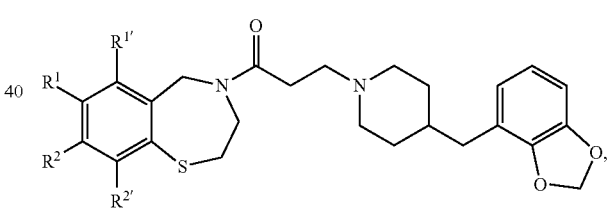

(12)

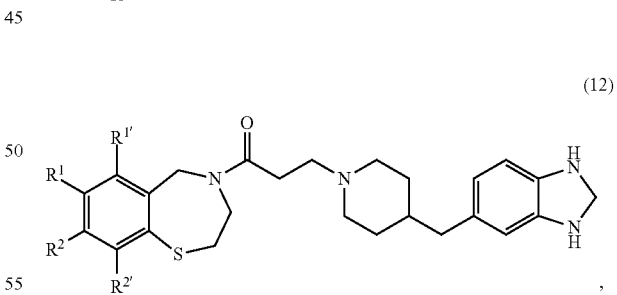

(13)

(14)
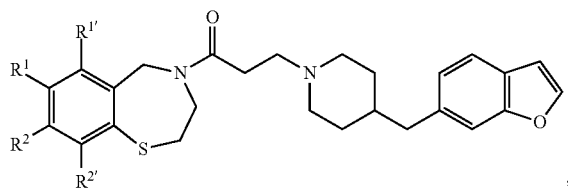
,

(15)
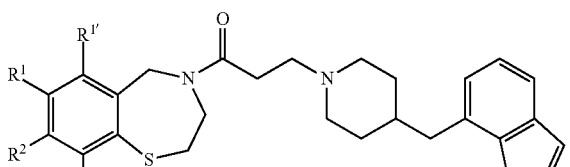
,

(16)
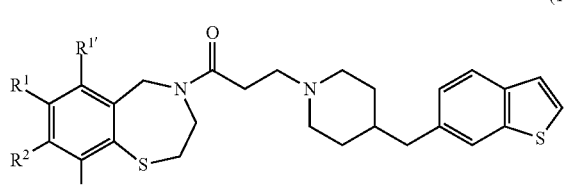
,

(17)
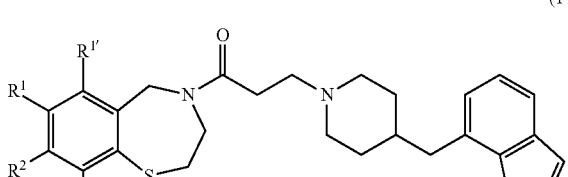
,

(18)
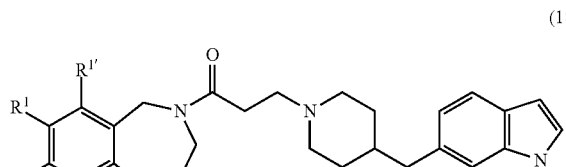
,

(19)
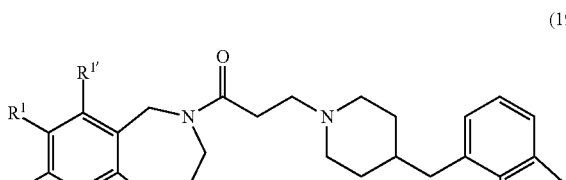
,

(20)
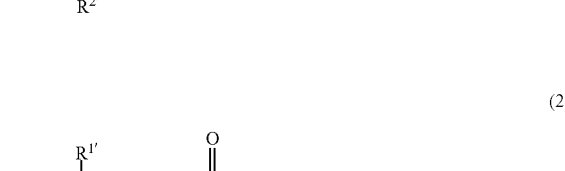
,

(21)
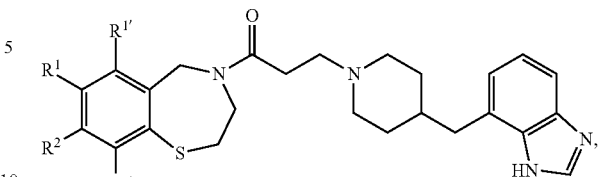
,

(22)
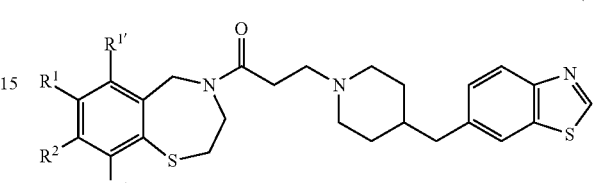
,

(23)
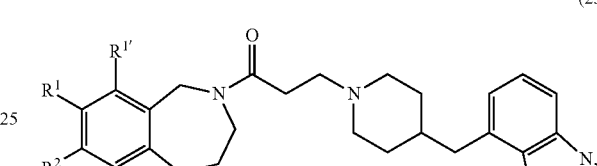
, where each of $R^1$, $R^{1'}$, $R^2$, and $R^{2'}$ independently is H or an electron-donating group. In some of these embodiments, each of $R^1$, $R^{1'}$, $R^2$, and $R^{2'}$ is H. In other embodiments, at least one of $R^1$, $R^{1'}$, $R^2$, and $R^{2'}$ is an electron-donating group selected from OH, $OR^4$, SH, $SR^4$, $NH_2$, $NHR^4$, $NR^4R^{4'}$, and a $C_{1-10}$ alkyl group optionally substituted with 1-4 groups independently selected from OH, $OR^4$, SH, $SR^4$, $NH_2$, $NHR^4$, and $NR^4R^{4'}$, where $R^4$ and $R^{4'}$ are as defined herein. For example, $R^1$ can be $OCH_3$, and $R^{1'}$, $R^2$, and $R^{2'}$ independently can be H or an electron-donating group as described herein. In particular embodiments, the present teachings provide the compounds:

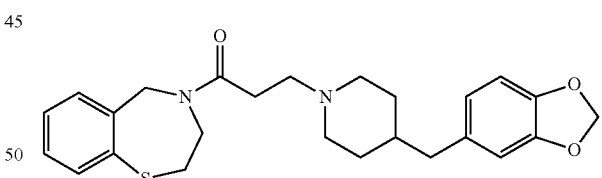
,

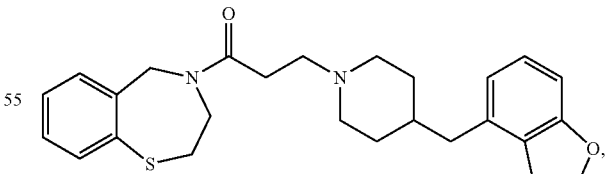
,

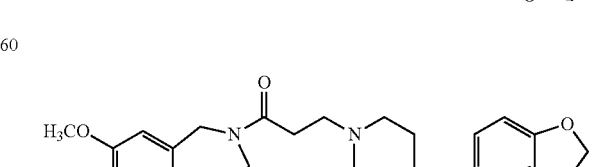
,

-continued

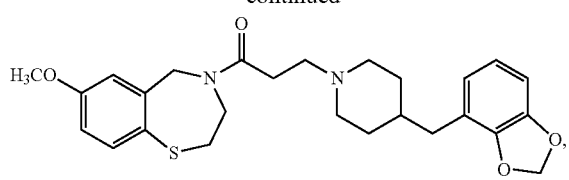

In some embodiments, the present compounds can have the formula:

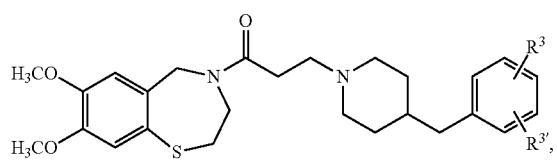

wherein $R^3$ and $R^{3'}$ are as defined herein. For example, $R^3$ and $R^{3'}$, independently can be selected from H, OH, $OR^4$, $NH_2$, $NHR^4$, and $NR^4R^{4'}$, where $R^4$ and $R^{4'}$ are as defined herein. In one particular embodiment, the present teachings provide the compound:

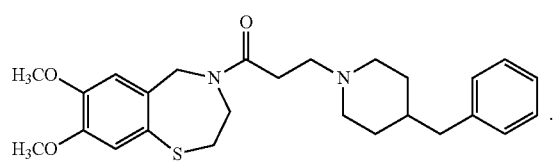 [SMILES: COc1cc2c(cc1OC)SCCN(C(=O)CCN1CCC(Cc3ccccc3)CC1)C2]

It should be understood that the present teachings can exclude certain embodiments of compounds having the formula:

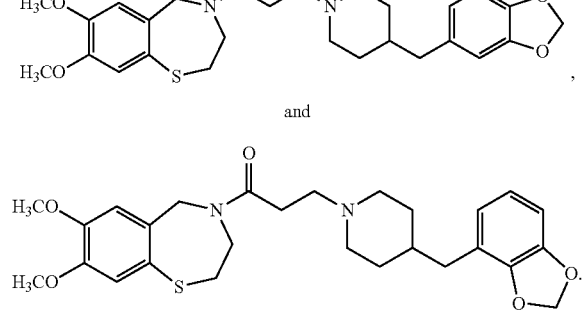

where $R^1$, $R^{1'}$, $R^2$, $R^{2'}$, $R^3$, and $R^{3'}$ are as defined herein. For example, the present teachings can exclude certain compounds where $R^1$ is —$OCH_3$, $R^3$ is $NH_2$, $R^{3'}$ is H or $NH_2$, and each of $R^{1'}$, $R^2$, and $R^{2'}$ is H. The present teachings also can exclude the compound where $R^1$ is OH, and each of $R^{1'}$, $R^2$, $R^{2'}$, $R^3$ and $R^{3'}$ is H.

In another aspect, the present teachings relate to derivatives of 4-chloro-m-cresol (4-CmC), a known activator of ryanodine receptors. More specifically, such derivatives can include one or more electron-donating groups in place of the chloro group, the methyl group, and/or one or more hydrogen atoms on the phenol. Applicants have found that by replacing the electron-withdrawing chloro group with an electron-donating group, the derivative can act as an inhibitor, instead of an activator, of ryanodine receptors.

Accordingly, the present teachings can relate to compounds of Formula II:

$$HO-\phantom{X}-X \qquad\qquad II$$
$$\phantom{HO-}CH_3$$

wherein X is an electron-donating group. For example, in certain embodiments, X can be selected from OH, $OR^5$, SH, $SR^5$, $NH_2$, $NHR^5$, $NR^5R^{5'}$, and a $C_{1-10}$ alkyl group optionally substituted with 1-4 groups independently selected from OH, $OR^5$, SH, $SR^5$, $NH_2$, $NHR^5$, and $NR^5R^{5'}$, where $R^5$ and $R^{5'}$ are identical or different $C_{1-10}$ alkyl groups. For example, $R^5$ and $R^{5'}$ independently can be selected from a methyl group, an ethyl group, an n-propyl group, an iso-propyl group, an n-butyl group, an iso-butyl group, a sec-butyl group, a tert-butyl group, an n-pentyl group, an iso-pentyl group, and an neopentyl group.

In certain embodiments, X can be selected from OH, $OR^5$, SH, $SR^5$, $NH_2$, $NHR^5$, and $NR^5R^{5'}$, where $R^5$ and $R^{5'}$ are as defined herein. In particular embodiments, X can be an alkoxy group. In particular embodiments, X can be $NH_2$, $NHR^5$, or $NR^5R^{5'}$, where $R^5$ and $R^{5'}$ are methyl groups. For example, the present teachings provide the compound

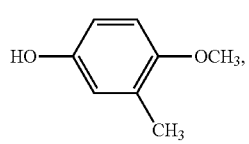

which is 4-methoxy-3-methylphenol and can be referred herein as 4-MmC.

Without wishing to be bound by any particular theory, compounds of the present teachings are believed to be able to inhibit activity of CRC because of their enhanced electron-donating properties. As electron donors, the present compounds are believed to shift the redox potential of reactive thiols on the RyR/CRC to more positive values and/or increase the number of reactive thiols on the RyR/CRC. It is further believed that these compounds can transiently exchange electrons with the Ca$^{2+}$ release protein and shift the thiol-disulfide balance within CRC.

More specifically, it has been demonstrated that there exists a class of hyperreactive thiols on RyR1 which are exposed when the Ca$^{2+}$ release channel is in the closed configuration. For example, using 7-diethylamino-3-(4'-maleimidyl-phenyl)-4-methylcoumarin (CPM), which fluoresces when it reacts with thiols, it has been found that the rate of CPM fluorescence increases ~10-fold in the closed configuration of the CRC. It has been recently identified that there are seven hyperreactive thiols per monomeric receptor unit, one of which (cys 3635) had previously been identified as the binding site for NO and calmodulin. It also has been shown that these hyperreactive thiols have a well-defined redox potential which is sensitive to the open versus closed state of the CRC, and which can be determined by measuring the rate of ryanodine binding as a function of the redox potential of the solution in which the assay is being carried out.

Accordingly, the effect of the present compounds as channel inhibitors can be directly observed as a shift in the redox potential of reactive thiols associated with the RyR. To illustrate, FIG. 1 shows the rate of ryanodine binding plotted versus the redox potential (mV) of a tested compound (control, caffeine, and tetracaine) in solution, which is defined as: $E_{sol}=-240+(2.3 \, RT/nF)^*\log_{10}[GSSG]/[GSH]^2$; where R is the gas constant, T is the temperature in K, n is the number of electrons transferred (n=2), F is the Faraday. A more positive solution potential is more oxidizing, while a more negative solution potential is more reducing. The redox potential of these reactive thiols is defined as the potential at which half of the thiols are oxidized and half are reduced—the midpoint of the redox titration. In a control experiment carried out with 20 μM Ca$^{2+}$, the redox potential=−160.3±3.2 mV. When caffeine (2 mM), a known channel activator and an electron acceptor, was added, the redox potential of the reactive thiols shifted to −197.8±5.8 mV, a more negative redox potential which favors the oxidation of these thiols. In contrast, when tetracaine (25 μM), a known channel inhibitor and an electron donor, was added, the redox potential of these thiols shifted to a more positive value (−147.7±2.8 mV), which favors the reduced state of these thiols. The shift in the redox potential of these thiols to a more reduced state by tetracaine is also evident from measurements of the total number of accessible thiols on the ryanodine receptor. In experiments where RyR1 receptors were isolated and the total number of thiols were measured using the CPM fluorescence technique described above, ~47 thiols per monomeric receptor were measured in control, untreated receptors. This is in good agreement with measurements reported in Sun et al., "Classes of thiols that influence the activity of the skeletal muscle calcium release channel," *J. Biol. Chem.* (2001); 276: 15625-15630. When caffeine was added, the number of thiols decreased to ~20 at 1 mM caffeine—presumably caused by oxidation of thiols to the disulfide form. In contrast, when tetracaine was added the number of thiols increased to ~70 per monomer at 10 mM tetracaine. See Marinov et al., "Non-thiol reagents regulate ryanodine receptor function by redox interactions that modify reactive thiols," *Antioxid. Redox. Signal*. (2007), 9: 609-621. As such, observations of a shift in the redox potential of reactive thiols on the RyR/CRC to more positive values and/or observations of an increase in the number of reactive thiols when RyRs are contacted with the present compounds would collaborate that the present compounds are donating electrons to the RyR channels, and as a result, inhibiting RyR channel activity.

Figure 6:
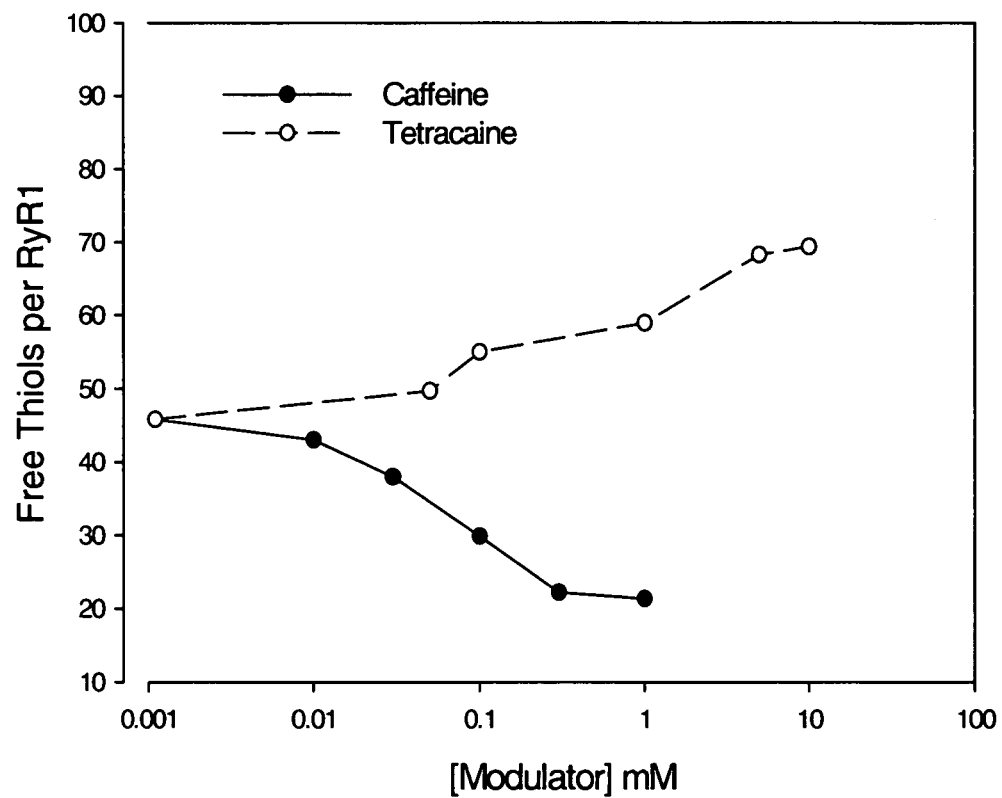
FIG. 6 correlates the total number of thiols on an isolated RyR1 that reacted with the fluorescent maleimide CPM (10 μM) in the presence of caffeine and tetracine, respectively.

The shift in the redox potential of reactive thiols to a more reduced state by tetracaine (FIG. 1) is also evident from measurements of the total number of accessible thiols on the ryanodine receptor (FIG. 6). In these experiments (Example 6), RyR1 was isolated and the total number of thiols that react with the fluorescent maleimide CPM (10 μM) was measured under various conditions. In the control, untreated receptor, ~47 thiols were measured per monomeric receptor, which is in good agreement with previous measurements [J. Sun, L. Xu, J. P. Eu, J. S. Stamler and G. Meissner, *Classes of thiols that influence the activity of the skeletal muscle calcium release channel*. J Biol Chem 276, 15625-15630 (2001)]. When the electron acceptor caffeine (1 mM) was added, the number of accessible thiols decreased to ~20; presumably caused by oxidation of thiols to the disulfide form. In contrast, when the electron donor tetracaine (10 mM) was added, the number of thiols increased to ~70 per monomer. Without wishing to be bound to any particular theory, this appears to be caused by reduction of endogenous disulfides to the SH form and suggests that a large number of thiols are oxidized during activation of the CRC by caffeine. However, in the range of tetracaine concentrations that inhibits ryanodine binding and single channel activity (0.1 to 0.5 mM), a relatively small number of additional thiols were measured by the fluorescent maleimide CPM. Although conformational changes may occur during exposure to tetracaine and/or caffeine, it is unlikely that the large changes in the number of thiols shown in FIG. 6 were caused by conformational changes. Without wishing to be bound to any particular theory, it is believed that tetracaine is transiently reducing protein disulfides to thiols, while caffeine is oxidizing thiols to disulfides. It should be emphasized that the shift in the redox potential (FIG. 1) and the SH/S—S balance (FIG. 6) are reversible.

The mechanisms proposed above by which the present compounds may inhibit CRC activity are not intended to be limiting, and the present compounds can achieve inhibition of CRC activity via other physical, chemical, and/or biological reactions including those described hereinbelow.

The efficacy of the present compounds to inhibit the activity of Ca$^{2+}$ release channels has been demonstrated by measuring the single channel activity of the CRC using procedures described in Example 4, and observing a decrease in the open probability of RyRs.

Figure 2:
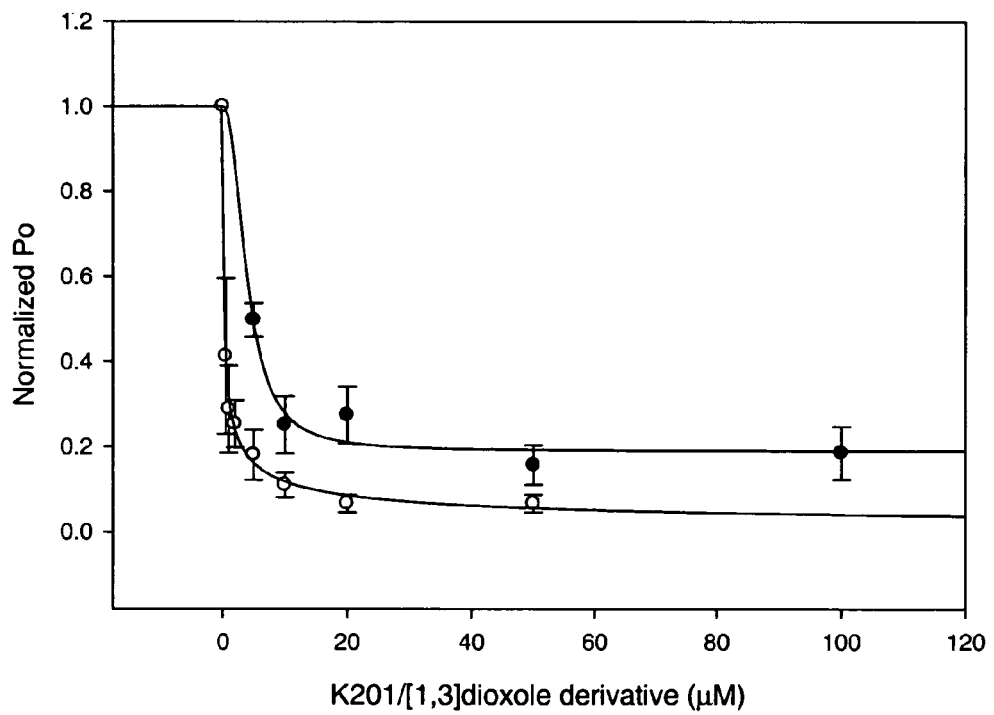
FIG. 2 compares the $IC_{50}$ of K201 versus the $IC_{50}$ of a [1,3]dioxole derivative of K201 according to the present teachings for inhibiting the single channel activity of CRC from skeletal muscle isolated from a rabbit. Open probability normalized to 1.0 for control is plotted vs. [K201] (●), and vs. the concentration of the [1,3]dioxole derivative (○).

Most notably, as demonstrated in FIG. 2, a [1,3]dioxole derivative of K201 (a compound of Formula I)

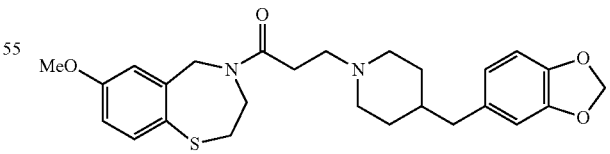

has been observed to exhibit an ability to inhibit single channel activity of skeletal muscle CRC that is ~16 times more potent than K201. Specifically, the concentration of K201 required to half maximally inhibits channel activity (IC$_{50}$, derived from a four parameter logistic curve fit from Sigma Plot) was determined to be 3.98±0.79 μM, while for the [1,3]dioxole derivative, the IC$_{50}$ was observed to be about 16 times lower (IC$_{50}$=0.24±0.05 μM). In vivo data obtained with this derivative also demonstrate its efficacy in inhibiting cardiac receptors RyR2.

Figure 3:
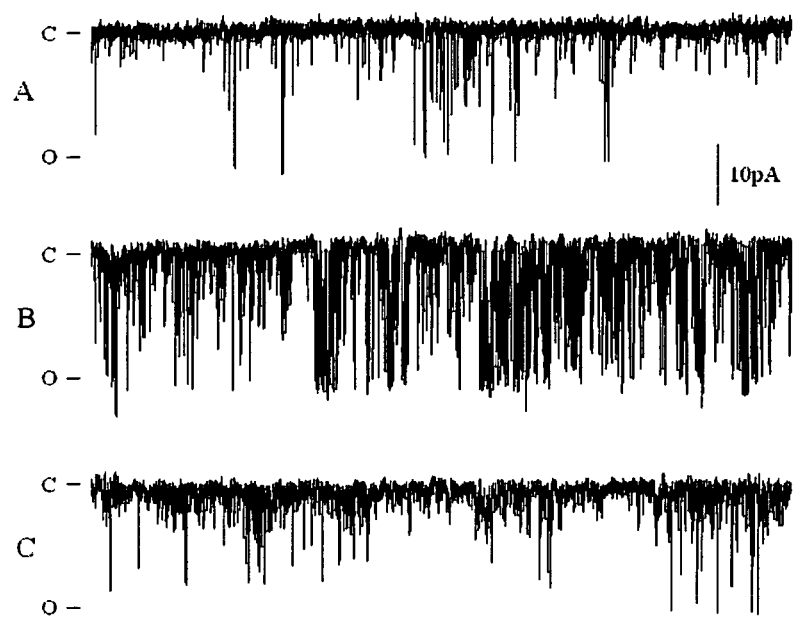
FIG. 3 shows inhibition of skeletal muscle CRC by 4-MmC.
Figure 5:
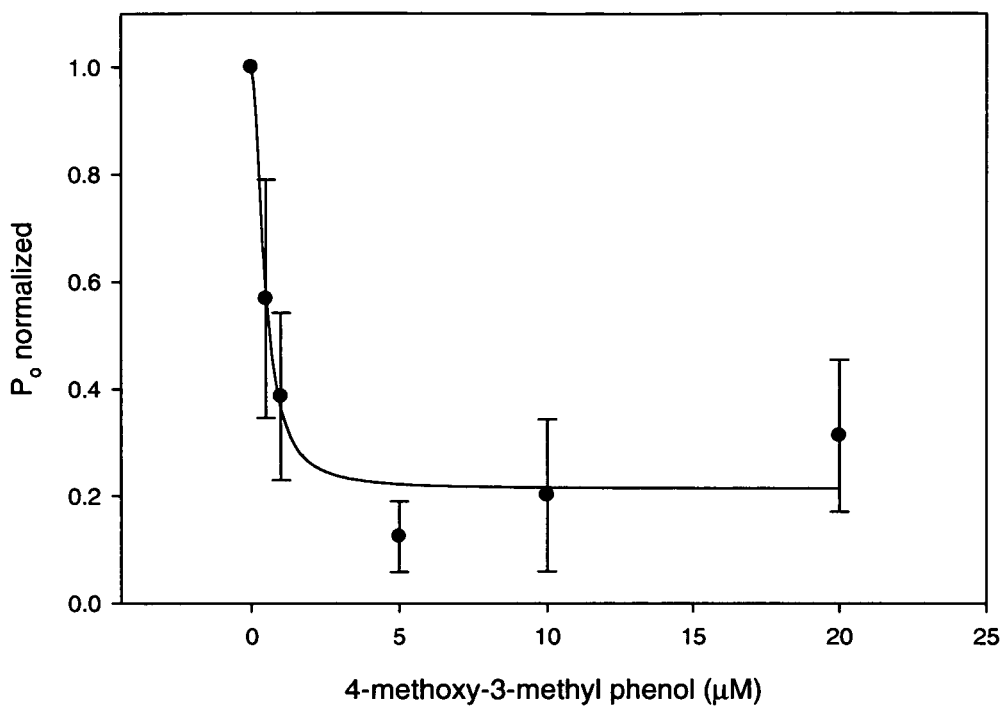
FIG. 5 plots the normalized open probability ($P_o$) of a single skeletal muscle CRC against sub-micromolar concentrations of 4-MmC. Data shown are mean±SE.

The inhibitory effects of compounds of Formula II on Ca$^{2+}$ release channels is demonstrated by FIGS. 3 and 5, which show that 4-methoxy-3-methylphenol or 4-MmC can significantly decrease the open probability (P$_o$) of skeletal muscle CRCs, including caffeine-activated skeletal muscle CRCs. Significant decrease in the open probability (P$_o$) of a single skeletal muscle CRC has been observed with a concentration of 4-MmC as low as 2 μM. These data show that by changing the 4-chloro group of 4-chloro-3-methylphenol (4-CmC) into a 4-methoxy group, the known CRC activator 4-CmC can be converted into an inhibitor of CRC activity.

The reduction in P$_o$ observed when a CRC is contacted with the present compounds suggests that the present compounds can be administered to limit, prevent, or treat intracellular Ca$^{2+}$ leak in a subject. Intracellular Ca$^{2+}$ leak and destabilization of the closed state of CRCs are known to be manifestations of a variety of skeletal and cardiac muscle conditions, disorders, and diseases. Accordingly, administration of the present compounds to a subject can be used to treat or reduce the risk of one or more of these conditions, disorders, and diseases in the subject.

For example, in heart failure, reduced myocardial contractility is observed. These contractile abnormalities result, in part, from alterations in the signaling pathway that allows the cardiac action potential to trigger Ca$^{2+}$ release via RyR2 channels and muscle contraction. In particular, in failing hearts, the amplitude of the whole-cell Ca$^{2+}$ transient is decreased and the duration prolonged.

Cardiac arrhythmia is a common feature of heart failure. In humans, atrial fibrillation (AF) is the most common cardiac arrhythmia. Structural and electrical remodeling, including shortening of atrial refractoriness, loss of rate-related adaptation of refractoriness, and shortening of the wavelength of re-entrant wavelets, can accompany sustained tachycardia. This remodeling is likely important in the development, maintenance and progression of atrial fibrillation. Studies suggest that calcium handling plays a role in electrical remodeling in atrial fibrillation.

While many victims of fatal ventricular arrhythmias and sudden cardiac death (SCD) are often otherwise-healthy individuals, catecholaminergic polymorphic ventricular tachycardia (CPVT) is an inherited disorder in individuals with structurally normal hearts. It is characterized by stress-induced ventricular tachycardia—a lethal arrhythmia that causes SCD. In subjects with CPVT, physical exertion and/or stress induce bidirectional and/or polymorphic ventricular tachycardias that lead to SCD even in the absence of detectable structural heart disease. CPVT is predominantly inherited in an autosomal-dominant fashion. Individuals with CPVT have ventricular arrhythmias when subjected to exercise, but do not develop arrhythmias at rest. Studies have identified mutations in the human RyR2 gene, on chromosome 1q42-q43, in individuals with CPVT.

Failing hearts (e.g., in patients with heart failure and in animal models of heart failure) are characterized by a maladaptive response that includes chronic hyperadrenergic stimulation. In heart failure, chronic beta-adrenergic stimulation is associated with the activation of beta-adrenergic receptors in the heart, which, through coupling with G-proteins, activate adenylyl cyclase and thereby increase intracellular cAMP concentration. cAMP activates cAMP-dependent PKA, which has been shown to induce hyperphosphorylation of RyR2. Thus, chronic heart failure is a chronic hyperadrenergic state which results in several pathologic consequences, including PKA hyperphosphorylation of RyR2.

The PKA hyperphosphorylation of RyR2 has been proposed as a factor contributing to depressed contractile function and arrhythmogenesis in heart failure. Consistent with this hypothesis, PKA hyperphosphorylation of RyR2 in failing hearts has been demonstrated, in vivo, both in animal models and in patients with heart failure undergoing cardiac transplantation.

In failing hearts, the hyperphosphorylation of RyR2 by PKA induces the dissociation of FKBP12.6 (calstabin2) from the RyR2 channel. This causes marked changes in the biophysical properties of the RyR2 channel, including increased open probability (Po) due to an increased sensitivity to Ca$^{2+}$-dependent activation; destabilization of the channel, resulting in subconductance states; and impaired coupled gating of the channels, resulting in defective EC coupling and cardiac dysfunction. Thus, PKA-hyperphosphorylated RyR2 is very sensitive to low-level Ca$^{2+}$ stimulation, and this manifests itself as a diastolic SR Ca$^{2+}$ leak through the PKA hyperphosphorylated RyR2 channel.

The maladaptive response to stress in heart failure results in depletion of FKBP12.6 from the channel macromolecular complex. This leads to a shift to the left in the sensitivity of RyR2 to Ca$^{2+}$-induced Ca$^{2+}$ release, resulting in channels that are more active at low-to-moderate Ca$^{2+}$ concentrations. Over time, the increased "leak" through RyR2 results in resetting of the SR Ca$^{2+}$ content to a lower level, which in turn reduces EC coupling gain and contributes to impaired systolic contractility.

Additionally, a subpopulation of RyR2 that are particularly "leaky" can release SR Ca$^{2+}$ during the resting phase of the cardiac cycle, diastole. This leads to depolarizations of the cardiomyocyte membrane known as delayed afterdepolarizations (DADs), which are known to trigger fatal ventricular cardiac arrhythmias.

In patients with CPVT mutations in their RyR2 and otherwise structurally-normal hearts, a similar phenomenon is at work. Specifically, it is known that exercise and stress induce the release of catecholamines that activate beta-adrenergic receptors in the heart. Activation of the beta-adrenergic receptors leads to PKA hyperphosphorylation of RyR2 channels. Evidence also suggests that the PKA hyperphosphorylation of RyR2 resulting from beta-adrenergic-receptor activation renders mutated RyR2 channels more likely to open in the relaxation phase of the cardiac cycle, increasing the likelihood of arrhythmias.

Cardiac arrhythmias are known to be associated with diastolic SR Ca$^{2+}$ leaks in patients with CPVT mutations in their RyR2 and otherwise structurally-normal hearts. In these cases, the most common mechanism for induction and maintenance of ventricular tachycardia is abnormal automaticity. One form of abnormal automaticity, known as triggered arrhythmia, is associated with aberrant release of SR Ca$^{2+}$, which initiates DADs. As described above, DADs are abnormal depolarizations in cardiomyocytes that occur after repolarization of a cardiac action potential. The molecular basis for the abnormal SR Ca$^{2+}$ release that results in DADs has not been fully elucidated. However, DADs are known to be blocked by ryanodine, providing evidence that RyR2 plays a key role in the pathogenesis of this aberrant Ca$^{2+}$ release.

Accordingly, RyR2 has been identified as a target for treating and preventing heart failure and cardiac arrhythmias, including atrial fibrillation and cardiac arrhythmias that cause exercise-induced SCD. RyR2 channels with 7 different CPVT mutations (e.g., S2246L, R2474S, N4104K, R4497C, P2328S, Q4201R, V4653F) were found to have functional defects that resulted in channels that became leaky (i.e., a calcium leak) when stimulated during exercise. The mechanism for the ventricular tachycardia (VT) in CPVT has been demonstrated to be the same as the mechanism for VT in heart failure.

It has been shown that exercise-induced arrhythmias and sudden death (in patients with CPVT) result from a reduced affinity of FKBP 12.6 (calstabin2) for RyR2. Additionally, it has been demonstrated that exercise activates RyR2 as a result of phosphorylation by adenosine 3',5'-monophosphate (cAMP)-dependent protein kinase (PKA). Mutant RyR2 channels, which had normal function in planar lipid bilayers under basal conditions, were more sensitive to activation by PKA phosphorylation—exhibiting increased activity (open probability) and prolonged open states, as compared with wild-type channels. In addition, PKA-phosphorylated mutant RyR2 channels were resistant to inhibition by $Mg^{2+}$, a physiological inhibitor of the channel, and showed reduced binding to FKBP12.6 (aka calstabin2, which stabilizes the channel in the closed state). These findings indicate that, during exercise, when the RyR2 are PKA-phosphorylated, the mutant CPVT channels are more likely to open in the relaxation phase of the cardiac cycle (diastole), increasing the likelihood of arrhythmias triggered by SR $Ca^{2+}$ leak.

Another major public health problem is the induction of often lethal arrhythmias triggered through a wide variety of drugs such as anti-histamines, antibiotics, psychiatric and cardiac drugs. Most of these pro-arrhythmic drugs inhibit the rapid component of the delayed rectifying $K^+$ current, $IK_r$, which is a major current responsible for the repolarization of the mammalian (including human) cardiac action potential (AP). The loss of function or reductions of $IK_r$ result in the prolongation of the AP and of the QT interval in the EKG and produces the cardiac phenotype called the long QT syndrome type 2 (LQT2). The general consensus is that the AP prolongation in LQT2 leads to the firing of early afterdepolarizations (EADs) that progress to a form of polymorphic ventricular tachyarrhythmia, called Torsade de Pointes (TdP). Although there is some controversy regarding the mechanisms that generate EADs, the dominant theory is that APD prolongation leads to $Ca^{2+}$ overload in the sarcoplasmic reticulum (SR) because $Ca^{2+}$ influx does not match $Ca^{2+}$ efflux. SR $Ca^{2+}$ overload leads to spontaneous SR $Ca^{2+}$ release, an enhanced Na—Ca exchange current (INCX) which causes abrupt depolarization of the membrane potential during the plateau phase which triggers the re-activation of L-type $Ca^{2+}$ channels. Intracellular $Ca^{2+}$ oscillations precede EADs, which lead to salvos of EADs and TdP. HERG poses a major challenge in terms of Safety Pharmacology because it is promiscuous and interacts readily with established and new drugs requiring extensive investigation to evaluate safety.

In vivo data (FIG. 12) obtained with electron-donating derivatives of K201 according to the present teachings have shown that the present derivatives can reverse arrhythmias induced by pro-arrhythmic drugs including $IK_r$ inhibitors.

Accordingly, the present teachings include use of the compounds disclosed herein as active therapeutic substances for the treatment of one or more conditions, disorders, and/or diseases which involve modulation of the RyR receptors, particularly the RyR1 and RyR2 receptors. As used herein, a ryanodine receptor (RyR) associated condition, disorder, or disease refers to a condition, disorder, or disease that can be treated and/or prevented by modulating the RyR receptors that regulate calcium channel functioning in cells. Examples of such ryanodine receptor (RyR) associated conditions, disorders, and diseases include various cardiac conditions, disorders, and diseases and skeletal muscle conditions, disorders, and diseases including those described herein.

RyR-associated cardiac conditions, disorders, and diseases include irregular heartbeat conditions, disorders, and diseases; drug-induced irregular heartbeat conditions, disorders, and diseases; exercise-induced irregular heartbeat conditions, disorders, and diseases; sudden cardiac death; drug-induced sudden cardiac death; exercise-induced sudden cardiac death; congestive heart failure; chronic obstructive pulmonary disease; and high blood pressure. Irregular heartbeat conditions, disorders, and diseases include drug-induced irregular heartbeat conditions, disorders, and diseases and exercise-induced irregular heartbeat conditions, disorders, and diseases which can include atrial and ventricular arrhythmia; atrial and ventricular fibrillation; atrial and ventricular tachyarrhythmia; atrial and ventricular tachycardia; catecholaminergic polymorphic ventricular tachycardia (CPVT); and drug- or exercise-induced variants thereof.

RyR-associated skeletal muscle conditions, disorders, and diseases include skeletal muscle fatigue, exercise-induced skeletal muscle fatigue, muscular dystrophy, bladder disorders, and incontinence.

Compounds of the present teachings can be prepared in different forms, such as salts, hydrates, complexes, esters, prodrugs or salts of prodrugs, and the present teachings include all variant forms of the compounds.

For example, a compound of the present teachings can be formulated as a pharmaceutically acceptable salt, e.g., acid addition salt, and complexes thereof. The preparation of such salts can facilitate the pharmacological use by altering the physical characteristics of the agent without preventing its physiological effect. Examples of useful alterations in physical properties include lowering the melting point to facilitate transmucosal administration and increasing the solubility to facilitate administering higher concentrations of the drug. Pharmaceutically acceptable salts of the compounds disclosed herein, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, benzenesulfonic, benzoic, camphorsulfonic, citric, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, naphthalenesulfonic, nitric, oxalic, pamoic, pantothenic, phosphoric, phthalic, propionic, succinic, sulfuric, tartaric, and toluenesulfonic, as well as other known pharmaceutically acceptable acids. In general, salt forms of the present compounds can be more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, can be used, for example, in the isolation of compounds of Formulae I and II for laboratory use or for subsequent conversion to a pharmaceutically acceptable salt.

Compounds of the present teachings also can form hydrates or solvates. The term "solvate" as used herein means a compound of Formula I or II, or a pharmaceutically acceptable salt of a compound of Formula I or II, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

Esters of the compounds disclosed herein can include various pharmaceutically acceptable esters known in the art that can be metabolized into the free acid form (e.g., a free carboxylic acid form) in a mammal. Examples of such esters include alkyl esters (e.g., of 1 to 10 carbon atoms), cycloalkyl esters (e.g., of 3-10 carbon atoms), aryl esters (e.g., of 6-14 carbon atoms, including of 6-10 carbon atoms), and heterocyclic analogues thereof (e.g., of 3-14 ring atoms, 1-3 of which can be selected from oxygen, nitrogen, and sulfur heteroatoms), wherein the alcohol residue can include further substituents. In some embodiments, esters of the compounds disclosed herein can be $C_{1-10}$ alkyl esters, such as methyl esters, ethyl esters, propyl esters, isopropyl esters, butyl esters, isobutyl esters, t-butyl esters, pentyl esters, isopentyl esters, neopentyl esters, and hexyl esters; $C_{3-10}$ cycloalkyl esters, such as cyclopropyl esters, cyclopropylmethyl esters, cyclobutyl esters, cyclopentyl esters, and cyclohexyl esters; or aryl esters, such as phenyl esters, benzyl esters, and tolyl esters.

Also provided in accordance with the present teachings are prodrugs of the compounds disclosed herein. As used herein, "prodrug" refers to a moiety that produces, generates or releases a compound of the present teachings when administered to a mammalian subject. Prodrugs can be prepared by modifying functional groups present in the compounds in such a way that the modifications are cleaved, either by routine manipulation or in vivo, from the parent compounds. For example, the compound can carry protective groups which are split off by hydrolysis in body fluids, e.g., in the bloodstream, thus releasing the active compound or is oxidized or reduced in body fluids to release the active compound. Examples of prodrugs include compounds as described herein that contain one or more molecular moieties appended to a hydroxyl, amino, sulfhydryl, or carboxyl group of the compound, and that when administered to a mammalian subject, is cleaved in vivo to form the free hydroxyl, amino, sulfhydryl, or carboxyl group, respectively. Examples of prodrugs can include acetate, formate, and benzoate derivatives of alcohol and amine functional groups in the compounds of the present teachings. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, the entire disclosures of which are incorporated by reference herein for all purposes. Prodrugs are often useful because, in some situations, they are easier to administer than the parent drug. They are bioavailable, for instance, by oral administration whereas the parent drug is not. The pro-drug also can have improved solubility in pharmaceutical compositions over the parent drug.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington: The Science and Practice of Pharmacy*, 20th edition, ed. Alfonso R. Gennaro, Lippincott Williams & Wilkins, Baltimore, Md. (2000), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be useful for treating a pathological condition, disease, or disorder in a subject. As used herein, "treating" refers to partially or completely alleviating and/or ameliorating the condition and/or symptoms thereof. The present teachings accordingly include a method of providing to a subject a pharmaceutical composition that includes a compound of the present teachings in combination or association with a pharmaceutically acceptable carrier. Compounds of the present teachings can be administered alone or in combination with other therapeutically effective compounds or therapies for the treatment of a pathological condition or disorder. As used herein, "therapeutically effective" refers to a substance or an amount that elicits a desirable biological activity or effect. As such, what is "therapeutically effective" depends upon the context in which it is being applied, and the activity or effective elicited can be preventive and/or therapeutic.

The terms "animal," "subject" and "patient" as used herein include all members of the animal kingdom including mammals (e.g., cats, dogs, horses, humans etc.).

Compounds of the present teachings can be administered to a subject by contacting target cells (e.g., cardiac muscle cells) in vivo in the subject with the compounds. The present compounds can be contacted with (e.g., introduced into) cells of the subject using known techniques utilized for the introduction and administration of proteins, nucleic acids and other drugs. Examples of methods for contacting the cells with (i.e., treating the cells with) the present compounds of Formula I can include absorption, electroporation, immersion, injection, introduction, liposome delivery, transfection, transfusion, vectors and other drug-delivery vehicles and methods. When the target cells are localized to a particular portion of a subject, it can be desirable to introduce the present compounds directly to the cells, by injection or by some other means (e.g., by introducing the compounds into the blood or another body fluid). The target cells can be contained in tissue of a subject and can be detected by standard detection methods readily determined from the known art, examples of which include immunological techniques (e.g., immunohistochemical staining), fluorescence imaging techniques, and microscopic techniques.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known antiinflammatory agents. Oral formulations containing an active compound disclosed herein can include any conventionally used oral form, including tablets, capsules, buccal forms, troches, lozenges and oral liquids, suspensions or solutions. In powders, the carrier can be a finely divided solid, which is an admixture with a finely divided active compound. In tablets, an active compound can be mixed with a carrier having the necessary compression properties in suitable proportions and compacted in the shape and size desired. The powders and tablets may contain up to 99% of the active compound.

Capsules can contain mixtures of active compound(s) with inert filler(s) and/or diluent(s) such as the pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Preferred surface modifying agents include nonionic and anionic surface modifying agents. Representative examples of surface modifying agents include poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the active compound(s). The oral formulation can also comprise a compound as described herein in water or fruit juice, containing appropriate solubilizers or emulsifiers as needed.

Liquid carriers can be used in preparing solutions, suspensions, emulsions, syrups, elixirs, and for inhaled delivery. A compound described herein can be dissolved or suspended in a pharmaceutically acceptable liquid carrier such as water, an organic solvent, or a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include water (particularly containing additives as described above, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, or granules. In such form, the pharmaceutical composition can be sub-divided in unit dose(s) containing appropriate quantities of the active compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form may contain from about 1 mg/kg of active compound to about 500 mg/kg of active compound, and can be given in a single dose or in two or more doses. Such doses can be administered in any manner useful in directing the active compound(s) to the recipient's bloodstream, including orally, via implants, parenterally (including intravenous, intraperitoneal and subcutaneous injections), and transdermally. Such administrations can be carried out using the compounds of the present teachings including pharmaceutically acceptable salts thereof, in lotions, creams, foams, patches, suspensions, and solutions.

When administered for the treatment or inhibition of a particular condition, disease state or disorder, it is understood that an effective dosage can vary depending upon many factors such as the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

Compounds described herein can be administered parenterally or intraperitoneally. Solutions or suspensions of these active compounds or pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In preferred embodiments, the form is sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, and esters thereof, in lotions, creams, foams, patches, suspensions, solutions, and suppositories (rectal and vaginal). Topical formulations that deliver active compound(s) through the epidermis can be useful for localized treatment of inflammation and arthritis.

Transdermal administration can be accomplished through the use of a transdermal patch containing an active compound and a carrier that can be inert to the active compound, can be non-toxic to the skin, and can allow delivery of the active compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active compound can also be suitable. A variety of occlusive devices can be used to release the active compound into the blood stream, such as a semi-permeable membrane covering a reservoir containing the active compound with or without a carrier, or a matrix containing the active compound. Other occlusive devices are known in the literature.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. The other agents can be administered at the same time or at different times than the compounds disclosed herein.

Compounds of the present teachings can be prepared in accordance with the procedures described in the examples below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, and/or by chromatography such as high performance liquid chromatography (HPLC) or thin layer chromatography.

Preparation of compounds can involve the protection and deprotection of various chemical groups. The need for protection and deprotection and the selection of appropriate protecting groups can be readily determined by one skilled in the art. The chemistry of protecting groups can be found, for example, in Greene, et al., *Protective Groups in Organic Synthesis,* 4th Ed., Wiley & Sons, 2006, the entire disclosure of which is incorporated by reference herein for all purposes.

The reactions of the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Aspects of the present teachings can be further understood in light of the following examples, which should not be construed as limiting the scope of the present teachings in any way.

EXAMPLE 1

Synthesis of 3-(4-(benzo[d][1,3]dioxol-5-ylmethyl)piperidin-1-yl)-1-(7-methoxy-2,3-dihydrobenzo[f][1,4]thiazepin-4(5H)-yl)propan-1-one

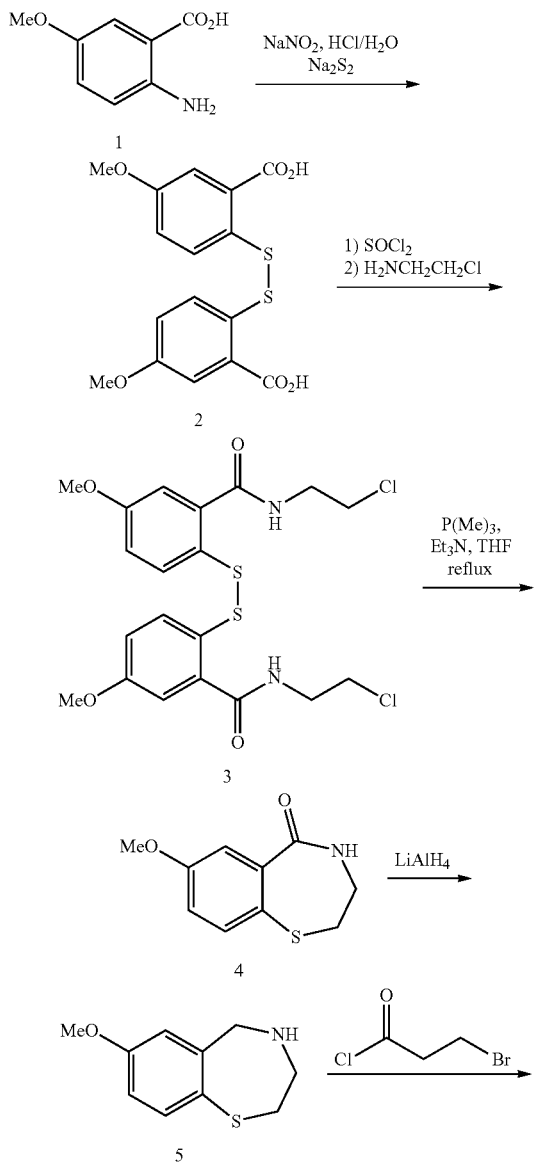

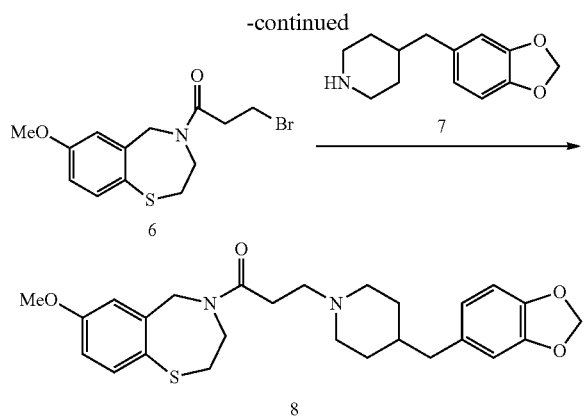

5-Methoxydithiosalicylic acid (compound 2)

2-Amino-5-methoxybenzoic acid (as purchased from Sigma-Aldrich) (compound 1, 5.0 g) was dissolved in H$_2$O (20 ml) and concentrated HCl (37.3%; 8 ml). The solution was cooled to −5° C. with a salt ice-H$_2$O bath and a solution of NaNO$_2$ (2.7 g) in H$_2$O (11 ml) was added slowly, maintaining the solution temperature below 5° C. The resulting mixture was stirred at 0° C. for 1 hour. The solution was filtered and added slowly at 0° C. to a solution of Na$_2$S$_2$ in H$_2$O prepared from Na$_2$S.9H$_2$O (10.3 g), sulfur (1.33 g), NaOH (1.6 g), and H$_2$O (16 ml). The reaction mixture was stirred at room temperature overnight and filtered. Upon acidification with concentrated HCl, the product was obtained as a solid.

5-Methoxydithiosalicylic acid di-2-chloroethyl amide (compound 3)

5-Methoxydithiosalicylic acid (3 g) was treated with SOCl$_2$ (5 ml) at reflux for 3 hours. Then, the excess SOCl$_2$ was removed under vacuum. The residue was dissolved in THF (150 ml) and cooled to 0° C., and 2-chloroethylamine hydrochloride (2.85 g) and Na$_2$CO$_3$ (5.2 g) were added. The resulting mixture was stirred at room temperature overnight. The solvents were removed. The residue was diluted with EtOAc, and the organic phase washed with H$_2$O, 1 N HCl, saturated NaHCO$_3$ and H$_2$O. After drying over Na$_2$SO$_4$ and removal of solvents a white solid was obtained.

7-Methoxy-5-oxo-2,3,4,5-tetrahydro-1,4-benzothiazepine (compound 4)

5-Methoxydithiosalicylic acid di-2-chloroethyl amide (2.0 g) in THF/methanol/H$_2$O (110 ml, 5:5:1) was treated with triethylamine (6 ml) and trimethylphosphine (18 mmol) at reflux for 12 hours. After removal of solvents, the residue was distributed into EtOAc and washed with saturated NaHCO$_3$ in H$_2$O. After column purification the pure product was obtained as a solid.

7-Methoxy-2,3,4,5-tetrahydro-1,4-benzothiazepine (compound 5)

7-Methoxy-5-oxo-2,3,4,5-tetrahydro-1,4-benzothiazepine (0.300 g) was treated with LiAlH$_4$ (0.160 g) in THF (10 ml) at reflux overnight. The mixture was cooled to room temperature and Na$_2$SO$_4$.10H$_2$O was added slowly to quench the reaction. The resulting mixture was stirred at room temperature for 1 hour and filtered through a short celite column. Removal of the solvents led to the desired product as a colorless oil.

4-(3-Bromopropionyl)-7-methoxy-2,3,4,5-tetrahydro-1,4-benzothiazepine (compound 6)

To a stirred solution of 7-methoxy-2,3,4,5-tetrahydro-1,4-benzothiazepine (0.250 g) and triethyl amine (0.53 g) in THF (10 ml) at 0° C. was added dropwise 3-bromopropionic chloride (0.444 g). The resulting mixture was stirred at 0° C. for 1 hour and at room temperature overnight. After dilution with ethyl acetate, the organic phase was washed with saturated NaHCO$_3$/H$_2$O and H$_2$O. After drying over sodium sulfate and filtration, removal of solvent gave to the product.

3-(4-(benzo[d][1,3]dioxol-5-ylmethyl)piperidin-1-yl)-1-(7-methoxy-2,3-dihydrobenzo[f][1,4]thiazepin-4(5H)-yl)propan-1-one (compound 8)

The reaction mixture of 6 (0.100 g), 4-benzo[1,3]dioxol-5-ylmethyl-piperidine (compound 7, as purchased from Bioblocks Inc., 0.086 g) and Na$_2$CO$_3$ (0.086 g) in DMF (5 ml) was stirred at 60° C. for 12 hours. DMF was evaporated under vacuum and the product extracted with EtOAc, washed with H$_2$O and dried over anhydrous Na$_2$SO$_4$. After filtration and removal of solvents, the crude product was purified by column chromatography.

EXAMPLE 2

Synthesis of 4-(dialkylamino)-3-methylphenols

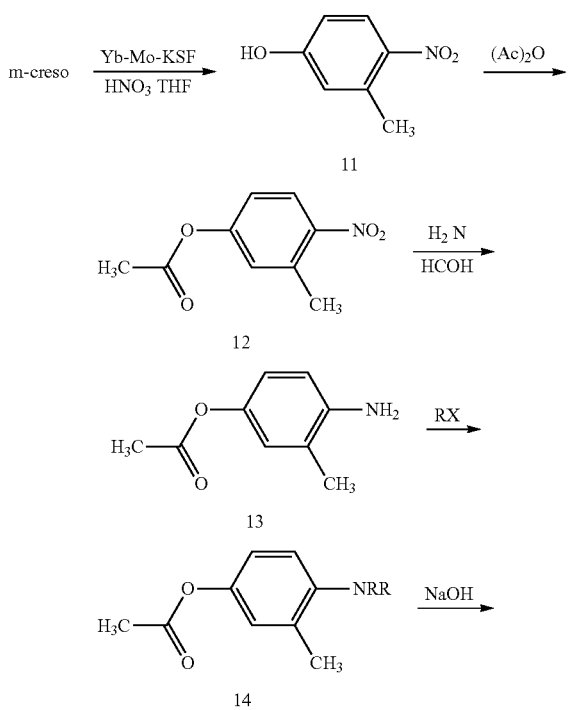

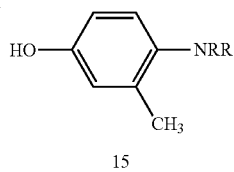

R and R = H or alky

Derivatives of 4-CmC (4-chloro-3-methylphenol) having increased electron donating properties can be obtained by preparing a series of 4-(dialkylamino)-3-methylphenol compounds as shown above. By varying R and R' groups on the amine, the compound's solubility and its electron donating ability can be fine-tuned.

The primary starting material, 11, can be prepared by nitration of m-cresol. An approach using Yb-doped montmorillonite KSF has been shown to provide the desired isomer in 52% yield. Reduction of the nitro group to form 12 can be performed with Raney Nickel. Final removal of acetate under basic conditions is expected to yield 15. Other derivatives can be prepared from 13 via Sandmeyer chemistry, turning the amino group into —CN, COOH (from hydrolysis of the nitrile), I, —SR(R=alkyl or aryl) and —OH.

EXAMPLE 3

Synthesis of 4-methoxy-3-methylphenol (4-MmC)

4-Methoxy-3-methylphenol was prepared according to the procedures described in Higgins et al., "An Assessment of the Reaction Energetics for Cytochrome P450-Mediated Reactions," *Arch. Biochem. Biophys.* (2001); 385: 220-30. Specifically, phosphorus oxychloride (5.1 ml, 0.057 mol) was added dropwise to a solution of o-methylanisole (5.33 ml, 0.043 mol) in dimethylformamide (6 g) under nitrogen. After addition, the mixture was heated and refluxed for 4 hours, cooled, and then added to 100 ml of water. To the solution, 10% NaOH was added and the solution was extracted with 4×100 ml of ether. The ether layers were washed with water and then brine solution, dried over magnesium sulfate, and evaporated under reduced pressure. The dark oil that remained (5.0 g, 77%) was purified by column chromatography (silica gel: 90% hexane, 10% ethyl acetate). The purified oil (1.78 g, 28%) was dissolved in dichloromethane (100 ml) and then 3.03 g (0.018 mol) 3-chloroperbenzoic acid was added. The mixture was refluxed under nitrogen for ~5 hours, cooled, and evaporated under reduced pressure. The residue was dissolved in ethyl acetate and washed with aqueous saturated sodium bicarbonate. The organic layer was dried over magnesium sulfate and evaporated under reduced pressured. The dark oil that remained was dissolved in 7 ml of methanol and 5.5 ml of 10% aqueous potassium hydroxide solution was added. The solution was stirred for ~2 hours, water was added, and the solution was extracted with ether. The ether layers were combined and washed with saturated sodium bicarbonate solution and then with water. The ether was dried over magnesium sulfate and evaporated under reduced pressure. The oil that remained (1.21 g, 74%) was recrystallized twice with hexane to give 4-methoxy-3-methyl-phenol as long white needles.

EXAMPLE 4

Single $Ca^{2+}$ Channel Analysis

Fast twitch skeletal muscle sarcoplasmic reticulum was isolated from New Zealand White rabbit, a rich source of skeletal receptors. Following isolation of a crude fraction, the SR was placed on a discontinuous sucrose gradient and a heavy fraction (HSR) was used for all single channel experiments. $Ca^{2+}$ release channel reconstitution into a bilayer membrane was carried out by the addition of SR vesicles to the cis side of a planar bilayer lipid membrane. Bilayers, made with a 5:3:2 mixture of phosphatidylethanolamine:phosphatidylserine:phosphatidylcholine (Avanti Polar Lipids) at 50 mg/ml in decane, were formed across a 150 μm hole drilled in a polystyrene cup separating two chambers of 0.7 ml each. The cis chamber contained 400 mM cesium methane sulfonate (CsMS), 50 μM $CaCl_2$, 25 mM HEPES, pH 7.4, while the trans side contained 40 mM CsMS, 25 mM HEPES pH 7.4. SR vesicles, suspended in 0.4-0.6 M sucrose, 400 mM CsMS were added to the cis chamber at a final concentration of 5-20 μg/ml. Following the fusion of a single vesicle, 4M CsMS, 25 mM Hepes, pH 7.4 was added to the trans chamber to equalize the CsMS concentration on the two sides of the membrane, which stopped further fusions. Channel activity was then measured at a holding potential of +25 mV with respect to the trans (ground) side. A Warner Instruments Bilayer Clamp Amplifier (model BC-525A) was used to amplify picoampere currents. The data were interfaced through a Digidata 1322A 16 bit data Acquisition System (Axon Instruments), stored filtered at 1 kHz and analyzed for single channel activity using pCLAMP software package (version 9.0, Axon Instruments, Burlingame, Calif.).

As shown in FIG. 5, 4-MmC significantly decreased the open probability ($P_o$) of the skeletal muscle CRC at submicromolar concentrations. Significant decrease was observed with a <5 μM concentration of 4-MmC, showing that 4-MmC is a potent inhibitor of channel activity, in this case, skeletal muscle CRC. The $K_i$ for inhibition of single channel activity was determined to be ~0.5

Figure 10:
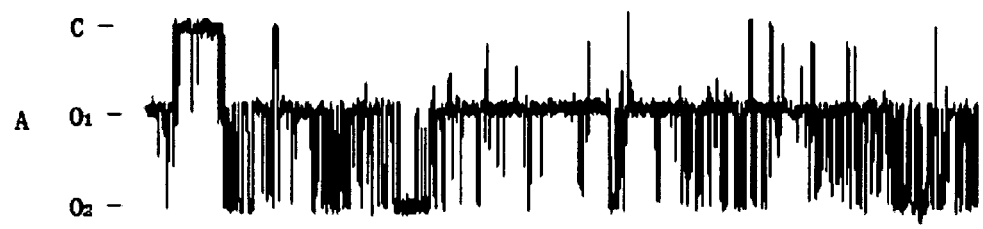
FIG. 10 shows inhibition of the cardiac receptor RyR2 by K201.
Figure 10:
Figure 10:

Generally speaking, most of the previously reported characteristics in the literature on the cardiac receptor (RyR2) are similar to that on the skeletal muscle receptor (RyR1). However, the sensitivity of RyR1 versus RyR2 to various agonists and antagonists occasionally differ. FIG. 10 measures the sensitivity of the cardiac receptor RyR2 to K201 at the single channel level, in which C represents the closed state, and $O_1$ and $O_2$, respectively, correspond to one or two open channels. In FIG. 2, the $IC_{50}$ for K201 inhibition of RyR1 is ~4.0 while in FIG. 10, addition of 0.5 μM K201 to RyR2 resulted in about 50% decrease in $P_o$ ($P_o$ is the open probability to state 1). Therefore, RyR2 (the cardiac receptor) appears to be significantly more sensitive (~8 fold) to inhibition by K201 than is RyR1 (the skeletal muscle receptor). Accordingly, it can be expected that a K201 derivative that inhibits the skeletal muscle receptor RyR1 will have even stronger inhibitory effects on the cardiac receptor RyR2.

EXAMPLE 5

Measuring Redox Properties of Channel Modulators

A sample buffer containing a compound to be tested and a photo-reactive dye (i.e., 10 μM methylene blue, eosin B or erythrosin B) can be continuously illuminated with white light (e.g., about 10 cm away from a halogen 20 W light source) and its spectral characteristics monitored as a function of time (e.g., using a HP8452A diode array spectrophotometer). This can be performed in the presence of oxygen. In general, oxygen dissolved in the solution may decrease the photochemical activity of the dye. To compensate and to increase the sensitivity of the method, a comparatively high light intensity can be used (e.g., in the range of about 1-3 mW/cm$^2$).

To determine if a compound is an electron acceptor, an electron donor (e.g., NADH or EDTA) can be added to the sample buffer to supply electrons to the photo-excited dye. The electron donor reduces the concentration of the dye cation radical and maintains an increased concentration of the dye anion radical. To test whether a compound is an electron donor, no separate electron donor is necessary. In both cases, a probe can be added (e.g., NBD-Cl or XTT) to react with superoxide and produce a detectable product. The product can be measured, for example, as an increase in absorbance at 470 nm. The difference between the probe absorbance at 470 nm in the presence of the compound to be tested and a control without the compound can be taken as a measure of redox activity of the compound.

When oxygen is unable to intercept all electrons from the dye anion radical, the dye anion radical may disproportionate and form a colorless compound. This process also may serve as a detectable variable corresponding to the redox activity of the tested compound. A compound with electron-acceptor properties intercepts electrons from dye anion radical and thus slows down the rate of dye photo-bleaching. A compound with electron-donor properties donates electrons to the dye cation radical, thus stabilizing the dye anion radical and increasing the rate of dye photo-bleaching. See also International Publication No. WO 2006/086670.

Figure 4:
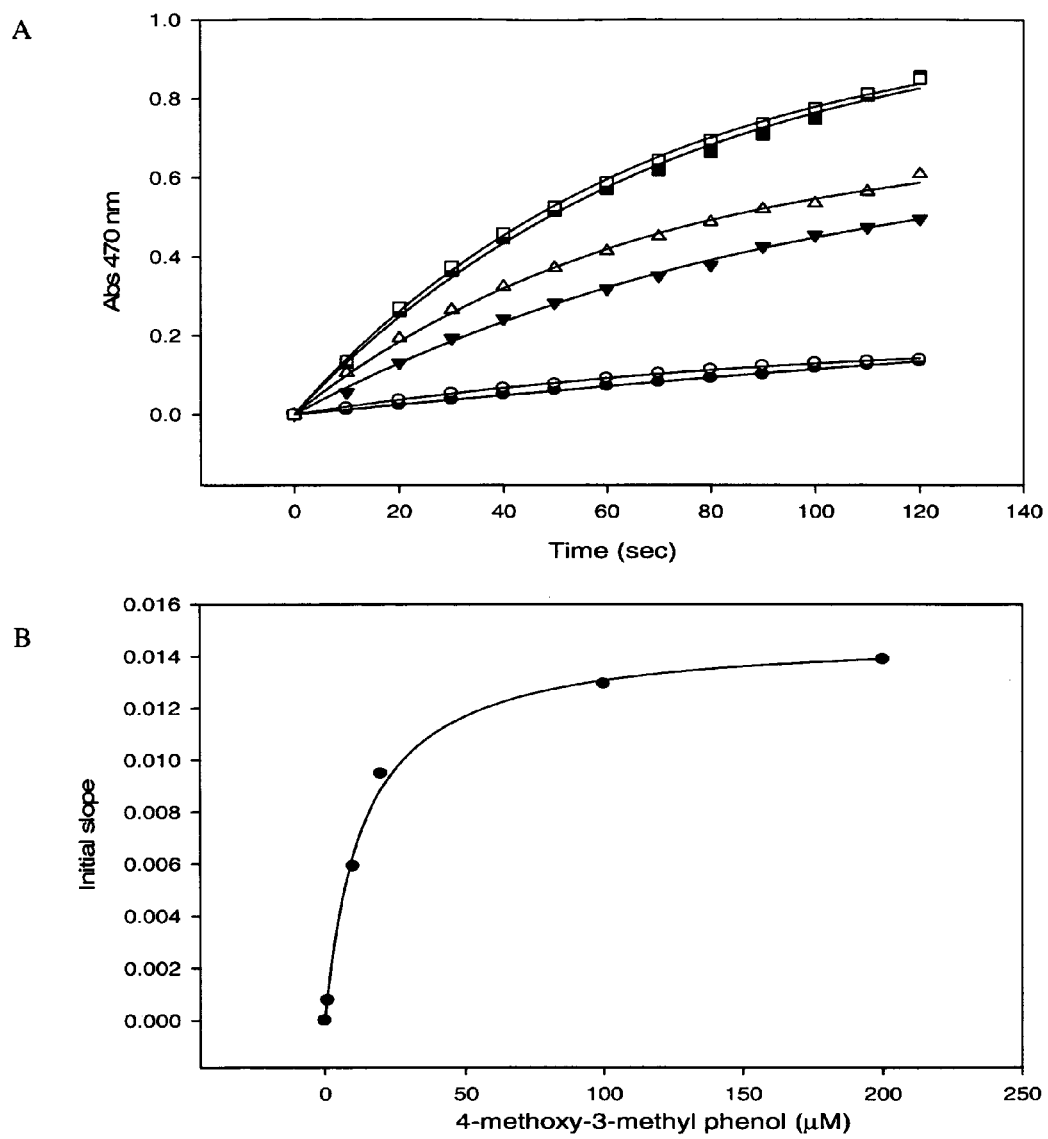
FIG. 4 demonstrates the electron donor activity of 4-MmC.

FIG. 4A shows the time-dependent reduction of XTT at different concentrations of 4-MmC. It can be seen that as the concentration of 4-MmC ws increased from 1 µM up to 200 µM, the rate and amount of reduction of XTT increased. In FIG. 4B, the initial rate of reduction of XTT is plotted versus the concentration of 4-MmC. The data were fit to the Michaelis-Menton equation. From these data, $K_d$, which corresponds to the concentration of 4-MmC at which half maximal electron donor activity is observed, was derived to be ~13 µM.

Figure 7:
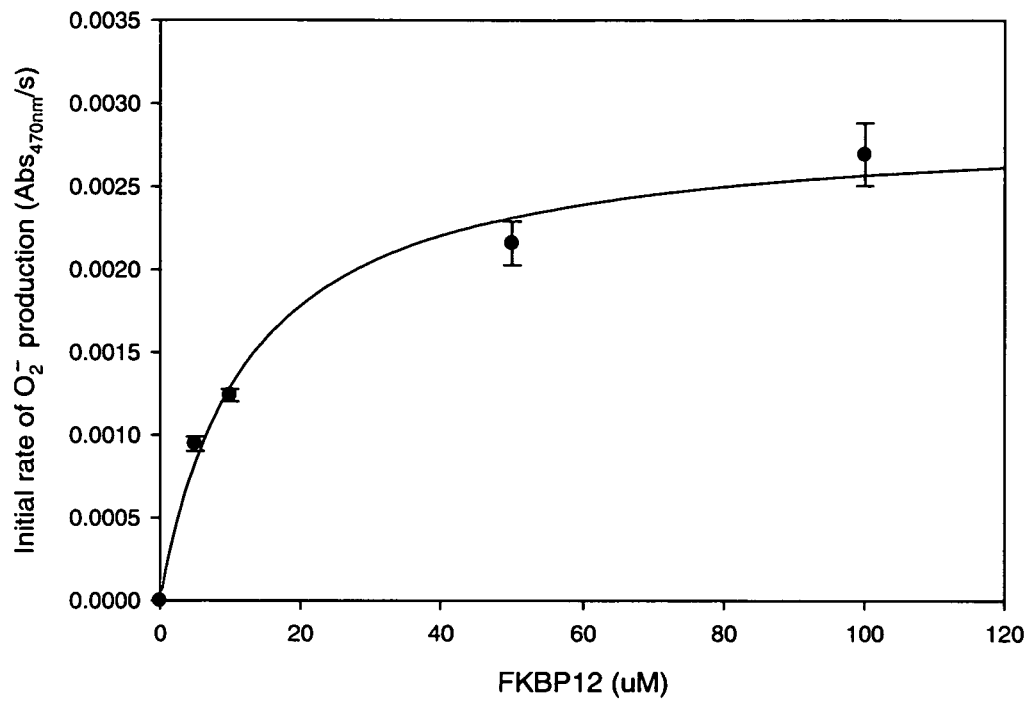
FIG. 7 demonstrates the electron donor activity of FKBP12 by plotting XXT reduction against increasing concentrations of FKBP12.

In addition, time-dependent measurements of XTT reduction were carried out in the presence of increasing concentrations of FKBP12 (5 µM to 100 µM). A series of exponential rise to maximum curves were obtained (similar to FIG. 4A). The initial rate of XTT reduction (which is proportional to the rate of $O_2^-$ production) is plotted versus the concentration of FKBP12 in FIG. 7. The data were fit to the Michaelis-Menton equation. The $K_d$ derived, which corresponds to the concentration of FKBP12, at which half maximal electron donor activity is observed ~12.4 µM. FIG. 7 shows that FKBP12 is a stronger electron donor than K201 ($K_d$=28 µM), but has similar electron donor properties to 4-methoxy-3-methyl phenol ($K_d$=13 µM, FIG. 4).

Figure 8:
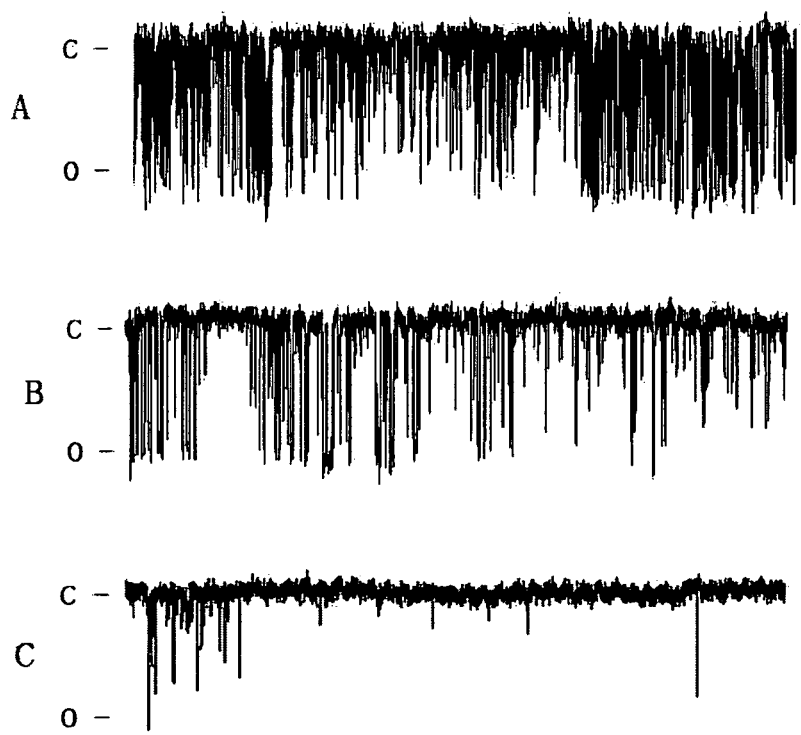
FIG. 8 shows inhibition of skeletal muscle CRC by K201.
Figure 9:
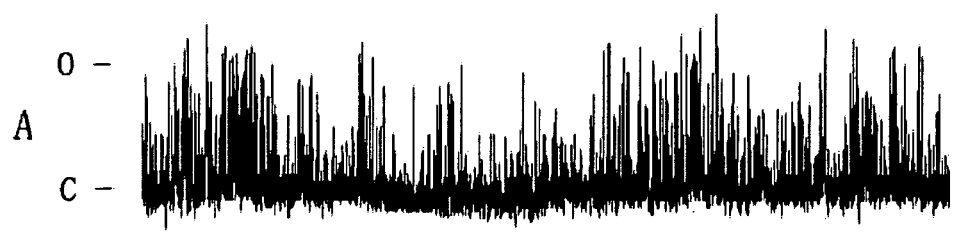
FIG. 9 shows inhibition of FK506-treated skeletal muscle CRC by K201.
Figure 9:
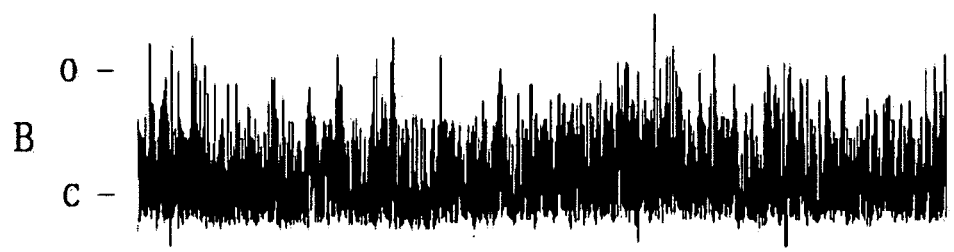
Figure 9:
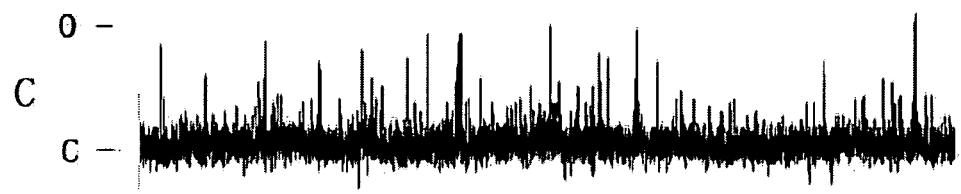

The hypothesis that K201 and other derivatives with strong electron donor properties inhibit single channel activity by virtue of their electron donor properties is supported by the data presented in FIGS. 8 and 9, obtained using procedures described in Example 5. As shown in FIGS. 8 and 9, K201 inhibits single channel open probability ($P_o$) both in the absence (FIG. 8) and presence of FK506 (FIG. 9). As expected, the $P_o$ increased when 20 µM FK506 was added to the cis chamber of the bilayer and the FKBP12 protein dissociates from the RyR complex. Even in the absence of the FKBP12 protein, subsequent addition of K201 (10 µM) still inhibited channel activity, even though it appeared to be somewhat less effective in decreasing the $P_o$ (FIG. 9).

Further, as shown in FIG. 9, removal of FKBP12 by addition of FK506, appears to have sensitized the RyR1 to oxidative stress by removing the endogenous electron donor FKBP12.

EXAMPLE 6

Measurement of Thiol Content of RyR Receptors

Isolated RyR receptors were suspended in a buffer containing 250 mM KCl, 15 mM NaCl, 20 mM Pipes, pH 7.1, with different concentrations of CRC modulators for 10 minutes at room temperature. The thiol-specific fluorescent probe CPM (10 µM) was added and incubated with the RyR receptors for 30 minutes. The final CPM fluorescence was measured at an excitation wavelength of 397 nm and an emission wavelength of 465 nm. Calibrations of the CPM fluorescence v. [GSH] were linear over the range of 0-5 µm GSH. The calculated number of thiols is normalized to the number of moles of RyR receptors.

EXAMPLE 7

In Vivo Data with K201 Derivative

In vivo data were obtained to show that derivatives of K201 that are stronger electron donors than K201 can be more effective than K201 in the treatment and/or prevention of conditions, disorders, and/or diseases which involve modulation of the RyR receptors.

Figure 11:
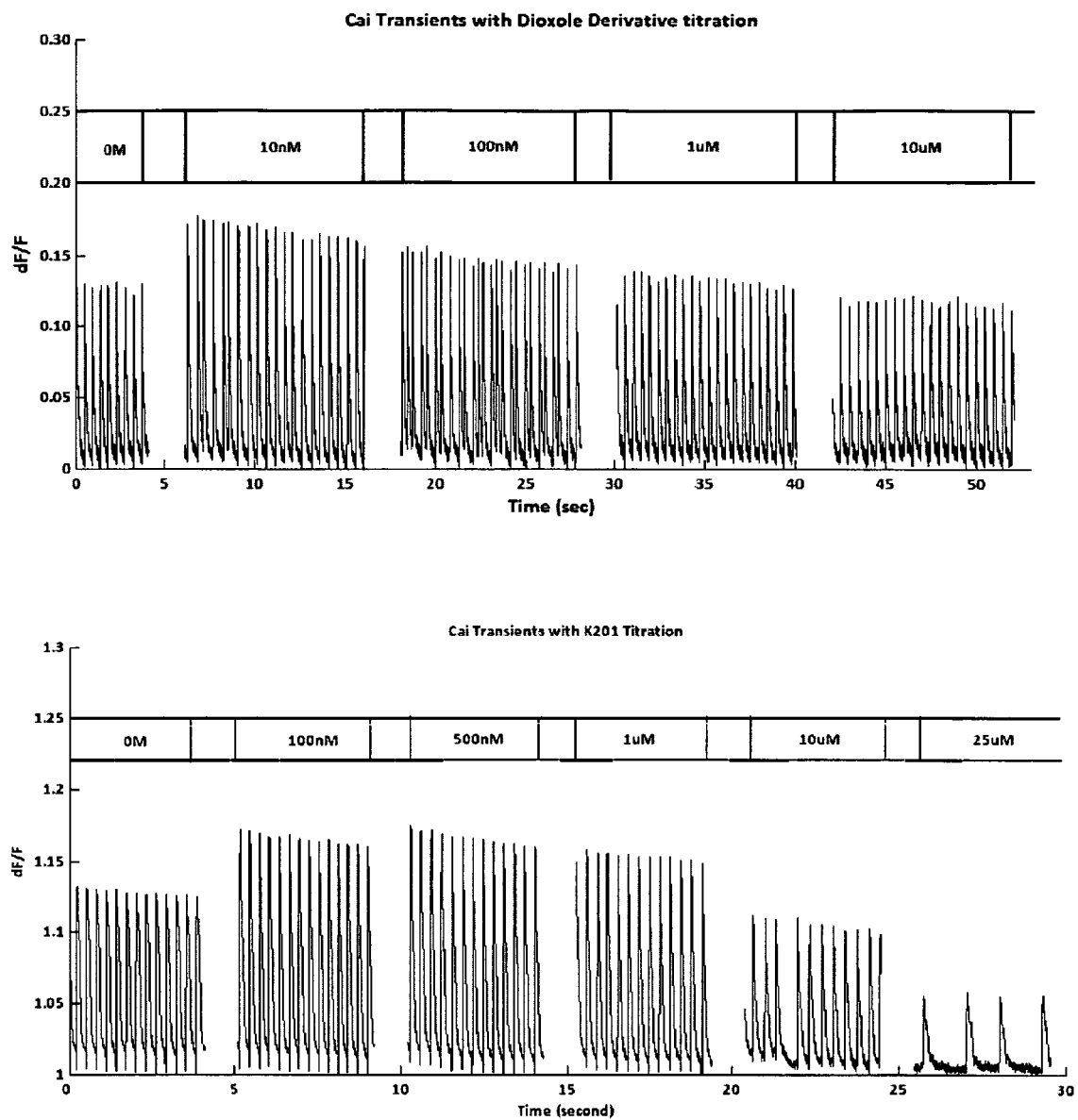
FIG. 11 shows that $Ca^{2+}$ transients are enhanced by the addition of a [1,3]dioxole derivative of K201 according to the present teachings (top). As comparison, enhancement of $Ca^{2+}$ transients by the addition of K201 is also shown (bottom).

FIG. 11 shows that $Ca^{2+}$ transients are enhanced by the addition of K201 and its dioxole derivative (Formula (10), where $R^1$ is $OCH_3$, and $R^{1'}$, $R^2$, and $R^{2'}$ are H). $Ca^{2+}_i$ transients were monitored in a Langendorff perfused mouse heart using Rhod-2 fluorescence.

In FIG. 11, both K201 and its dioxole derivative were shown to enhance $Ca^{2+}$ transients in female TNF-α perfused mouse hearts at nanomolar concentrations. Although TNF-α female hearts exhibit fewer premature ventricular beats and arrhythmias than their male littermates, they show a smaller $Ca^{2+}$ transient than do their WT counterparts. Reflecting the enhanced sensitivity of RyR2 to these two drugs, it was observed that the addition of the dioxole derivative of K201 at a concentration as low as 10 nM caused an enhancement of the fractional change in the fluorescence of Rhod-2, which corresponds to an increased rate and amplitude of $Ca^{2+}$ release from SR. It is believed that the faster and larger $Ca^{2+}$ transient is due to an increase in $Ca^{2+}$ load in the lumen of the SR caused by a reduced $Ca^{2+}$ "leak" from the SR. It is worth noting that the amplitude of the $Ca^{2+}$ transients were not adversely affected until the concentration of K201 reached 10-25 µM. In contrast, the dioxole derivative did not reduce the amount of SR $Ca^{2+}$ release compared to controls. Between each 5-10 second interval in which the fluorescence was displayed, there was a 10 minute period to allow the perfused heart to equilibrate with the new concentration of drug. The inhibition of $Ca^{2+}$ transients by high concentrations of K201 may be due to a direct interaction and inhibition of RyR2 channel opening or indirectly to its action on L-type $Ca^{2+}$ channels.

Figure 12:
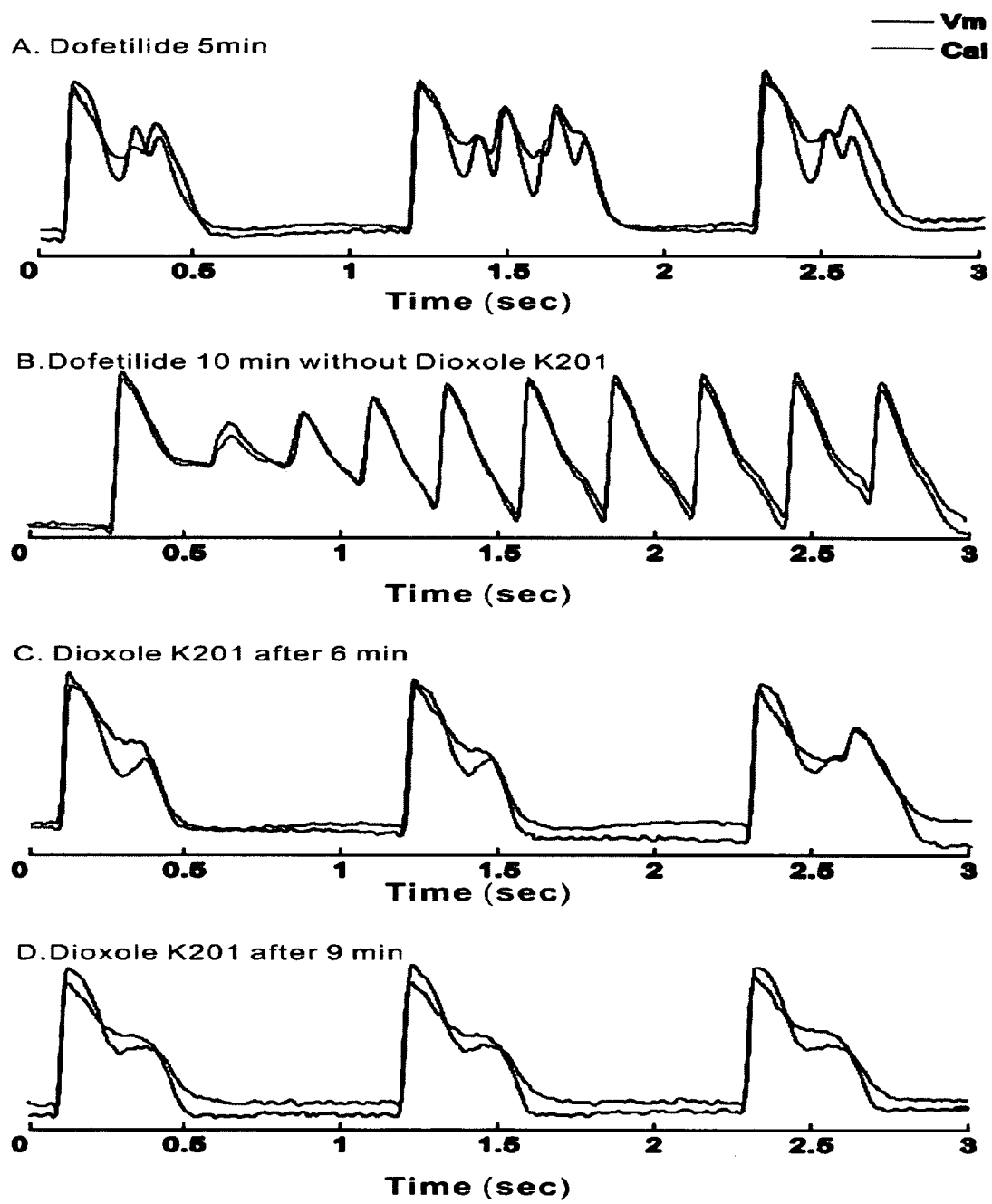
FIG. 12 shows that a [1,3]dioxole derivative of K201 according to the present teachings can reverse arrhythmias induced by selective $IK_r$ inhibitors such as dofetilide.

FIG. 12 shows that the dioxole derivative of K201 is an anti-arrhythmic agent and is protective of TdP in LQT2. Specifically, FIG. 12 shows that the dioxole derivative of K201 (1 µM) can reverse arrhythmias induced by dofetilide (0.5 µM).

Dofetilide, a selective $IK_r$ inhibitor, lengthens the cardiac AP, elicits EADs in 5 minutes (panel A) and promotes TdP (panel B) in Langendorff perfused rabbit hearts. EADs are triggered by spontaneous SR $Ca^{2+}$ release and increase in severity or frequency leading to TdP after a few minutes.

By adding 1.0 µM of the dioxole derivative of K201, all EADs were suppressed and the normal AP shape was restored (panels C and D). It is worth noting that the addition of the dioxole derivative of K201 eliminated both EADs and delayed afterdepolarizations (DADs). Furthermore, the protective effects lasted throughout or for 20 minutes of continuous perfusion with dofetilide and the dioxole derivative of K201. These data were derived from adult female rabbit hearts (n=3) that were paced at 1.2 second intervals.

In summary, the dioxole derivative of K201 was demonstrated to be a potent inhibitor of single channel activity (FIG. 2), and that it can increase $Ca^{2+}$ loading in TNF-α female mouse heart failure model (FIG. 11), and decrease arrhythmias in a rabbit heart following treatment with a $K^+$ channel inhibitor that induces long QT syndrome (FIG. 12). Other derivatives of K201 having enhanced electron donor properties can be expected to interact with the CRC and decrease the $Ca^{2+}$ leak associated with RyR2, which in turn can be used in possible treatment of long QT syndrome.

The inventors thank Professor Guy Salama of the Department of Cell Biology and Physiology at the University of Pittsburgh for providing FIGS. 11 and 12 and allowing their reproduction in the present application.

All publications, patent applications, patents, and other references mentioned herein are incorporated by reference in their entirety.

Variations, modifications, and other implementations of what is described herein will occur to those of ordinary skill in the art without departing from the spirit and the essential characteristics of the present teachings. Accordingly, the scope of the present invention is to be defined not by the preceding illustrative description but instead by the following claims, and all changes that come within the meaning and range of equivalency of the claims are intended to be embraced therein.

The invention claimed is:

1. A method for modulating a ryanodine receptor (RyR) that regulates calcium channel functioning in a cell, the method comprising contacting a cell with an effective amount of a compound having the formula

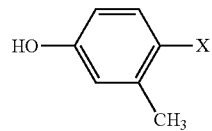

or a pharmaceutically acceptable salt, hydrate, ester, or prodrug thereof;

wherein X is an electron-donating group selected from OH, $OR^5$, SH, $SR^5$, $NH_2$, $NHR^5$, $NRSR^{5'}$, or a $C_{1-10}$ alkyl group substituted with 1-4 groups independently selected from OH, $OR^5$, SH, $SR^5$, $NH_2$, $NHR^5$, and NRSRS'; and $R^5$ and $R^{5'}$ are identical or different $C_{1-10}$ alkyl groups.

2. The method of claim 1 wherein X is —$OCH_3$.

3. The method of claim 1 wherein:
X is OH, $OR^5$, $NH_2$, $NHR^5$, or $NR^5R^{5'}$; and
$R^5$ and $R^{5'}$ independently are a methyl group, an ethyl group, an n-propyl group, an iso-propyl group, an n-butyl group, an iso-butyl group, a sec-butyl group, a tert-butyl group, an n-pentyl group, an iso-pentyl group, or a neo-pentyl group.

4. The method of claim 3 wherein $R^5$ and $R^{5'}$ are methyl.

5. The method of claim 1, wherein the effective amount is <5 μM.

6. The method of claim 5 wherein X is —$OCH_3$, and the effective amount is 2-5 μM.

7. The method of claim 1 wherein the compound modifies thiol/disulfide balance within ryanodine receptors in the cell.

8. The method of claim 1, wherein the cell is a muscle cell.

9. The method of claim 8 wherein the compound decreases intracellular $Ca^{2+}$ release in the muscle cell.

10. The method of claim 7 wherein the muscle cell is a skeletal muscle cell or a cardiac muscle cell.

11. The method of claim 8 wherein the compound reduces the open probability of ryanodine receptors in a skeletal muscle cell.

12. The method of claim 8 wherein the compound reduces the open probability of ryanodine receptors in a cardiac muscle cell.

* * * * *